US010595400B1

(12) United States Patent
Razaghi et al.

(10) Patent No.: US 10,595,400 B1
(45) Date of Patent: Mar. 17, 2020

(54) TAMPER DETECTION SYSTEM

(71) Applicant: Square, Inc., San Francisco, CA (US)

(72) Inventors: Mani Razaghi, San Francisco, CA (US); Jesse Hill, Daly City, CA (US)

(73) Assignee: Square, Inc., San Francisco, CA (US)

( * ) Notice: Subject to any disclaimer, the term of this patent is extended or adjusted under 35 U.S.C. 154(b) by 0 days.

(21) Appl. No.: 15/281,707

(22) Filed: Sep. 30, 2016

(51) Int. Cl.
| | |
|---|---|
| *G01R 27/08* | (2006.01) |
| *H05K 1/02* | (2006.01) |
| *H05K 1/18* | (2006.01) |
| *H05K 7/14* | (2006.01) |
| *H05K 5/02* | (2006.01) |
| *G01N 27/20* | (2006.01) |
| *G01N 17/00* | (2006.01) |
| *G01N 17/02* | (2006.01) |
| *G01L 1/10* | (2006.01) |
| *G01L 1/20* | (2006.01) |

(Continued)

(52) U.S. Cl.
CPC .......... *H05K 1/0275* (2013.01); *G01N 17/00* (2013.01); *G01N 17/006* (2013.01); *G01N 17/02* (2013.01); *G01N 27/20* (2013.01); *H05K 1/181* (2013.01); *H05K 5/0217* (2013.01); *H05K 7/1427* (2013.01); *G01L 1/10* (2013.01); *G01L 1/20* (2013.01); *G01L 1/22* (2013.01); *G01R 27/00* (2013.01); *H05K 2201/10151* (2013.01)

(58) Field of Classification Search
CPC ...... G01N 17/00; G01N 17/006; G01N 17/02; G01N 27/02; G01N 27/04; G01L 1/10; G01L 1/20; G01L 1/22; G01R 27/00

USPC .......... 324/76.11–76.83, 439, 459, 549, 600, 324/639, 649, 691, 693
See application file for complete search history.

(56) References Cited

U.S. PATENT DOCUMENTS

| | | | |
|---|---|---|---|
| 3,276,032 | A | 9/1966 | Ordower |
| 4,691,350 | A | 9/1987 | Kleijne et al. |

(Continued)

FOREIGN PATENT DOCUMENTS

| | | |
|---|---|---|
| DE | 195 12 266 A1 | 3/1996 |
| DE | 103 37 567 B3 | 1/2005 |

(Continued)

OTHER PUBLICATIONS

Balaban, D., "Google's Schmidt Predicts Contactless Terminal Rollout," NFC Times, published Jun. 23, 2011, Retrieved from the Internet URL: http://www.nfctimes.com/news/google-s-schmidt-predicts-contactless-terminal-rollout, on Aug. 25, 2015, pp. 1-4.

(Continued)

*Primary Examiner* — Raul J Rios Russo
(74) *Attorney, Agent, or Firm* — Lee & Hayes, P.C.

(57) ABSTRACT

A payment reader includes a tamper detection system having a first sensor element disposed on a circuit board of the tamper detection circuit; a second sensor element disposed within an interior surface of a housing of the tamper detection circuit; and a guard ring disposed on the circuit board of the tamper detection circuit configured to form an electrical connection with the first sensor element in response to injection of conductive fluid thereby indicating tampering with the tamper detection circuit, wherein the guard ring is configured to be on a plane different from the first sensor element to prevent unintentional activation of the tamper detection circuit.

20 Claims, 14 Drawing Sheets

(51) Int. Cl.
  *G01R 27/00* (2006.01)
  *G01L 1/22* (2006.01)

(56) References Cited

U.S. PATENT DOCUMENTS

| | | | |
|---|---|---|---|
| 4,811,288 | A | 3/1989 | Kleijne et al. |
| 5,233,505 | A | 8/1993 | Chang et al. |
| 5,574,600 | A | 11/1996 | Agro |
| 5,666,265 | A | 9/1997 | Lutz et al. |
| 5,880,523 | A | 3/1999 | Candelore |
| 6,084,905 | A | 7/2000 | Ishifuji et al. |
| 6,144,800 | A | 11/2000 | Kobayashi |
| 6,193,152 | B1 | 2/2001 | Fernando et al. |
| 6,230,972 | B1 | 5/2001 | Dames et al. |
| 6,234,389 | B1 | 5/2001 | Valliani et al. |
| 6,247,645 | B1 | 6/2001 | Harris et al. |
| 6,492,978 | B1 | 12/2002 | Selig et al. |
| 6,557,754 | B2 | 5/2003 | Gray et al. |
| 6,715,078 | B1 | 3/2004 | Chasko et al. |
| 7,049,970 | B2 | 5/2006 | Allen et al. |
| 7,343,496 | B1 | 3/2008 | Hsiang et al. |
| 7,373,667 | B1 | 5/2008 | Millard |
| 7,428,984 | B1 | 9/2008 | Crews et al. |
| 7,474,550 | B2 | 1/2009 | Fujisawa et al. |
| 7,806,341 | B2 | 10/2010 | Farooq et al. |
| 8,310,370 | B1 | 11/2012 | Williams, Jr. et al. |
| 8,701,997 | B2 | 4/2014 | Dorsey et al. |
| 9,203,546 | B1 | 12/2015 | Wade et al. |
| 9,298,956 | B2 | 3/2016 | Wade et al. |
| 9,449,192 | B1 | 9/2016 | Wade et al. |
| 9,578,763 | B1 | 2/2017 | Wade |
| 9,730,315 | B1* | 8/2017 | Razaghi ............... H05K 1/0275 |
| 9,852,422 | B1 | 12/2017 | Wade et al. |
| 9,913,778 | B2 | 3/2018 | Dvorak et al. |
| 10,140,604 | B1 | 11/2018 | Douthat et al. |
| 10,192,076 | B1 | 1/2019 | Razaghi |
| 10,251,260 | B1 | 4/2019 | Razaghi |
| 10,504,096 | B1 | 12/2019 | Hafemann et al. |
| 2001/0056542 | A1 | 12/2001 | Cesana et al. |
| 2002/0060869 | A1 | 5/2002 | Sawaguchi et al. |
| 2005/0039052 | A1 | 2/2005 | O'Donnell et al. |
| 2005/0191878 | A1* | 9/2005 | Castle ................... G08B 29/046 439/76.1 |
| 2005/0218229 | A1 | 10/2005 | Morley, Jr. et al. |
| 2005/0219728 | A1 | 10/2005 | Durbin et al. |
| 2005/0275538 | A1* | 12/2005 | Kulpa ..................... G06F 21/87 340/568.2 |
| 2006/0038011 | A1 | 2/2006 | Baker et al. |
| 2006/0102458 | A1 | 5/2006 | Kim et al. |
| 2006/0220850 | A1 | 10/2006 | Bowser et al. |
| 2006/0238301 | A1 | 10/2006 | Wu et al. |
| 2007/0131768 | A1 | 6/2007 | Wakabayashi |
| 2007/0271189 | A1 | 11/2007 | Morten et al. |
| 2007/0290845 | A1* | 12/2007 | Benjelloun ........... G08B 29/046 340/568.1 |
| 2007/0293142 | A1 | 12/2007 | Dehmas et al. |
| 2008/0110987 | A1 | 5/2008 | Cato et al. |
| 2008/0164320 | A1 | 7/2008 | Garrido-Gadea et al. |
| 2008/0278217 | A1* | 11/2008 | Hankhofer ........... H05K 1/0275 327/509 |
| 2008/0284610 | A1 | 11/2008 | Hunter |
| 2008/0309396 | A1* | 12/2008 | Lee .................. G06K 19/07372 327/509 |
| 2009/0070658 | A1 | 3/2009 | Patapoutian et al. |
| 2009/0291635 | A1 | 11/2009 | Savry |
| 2010/0034434 | A1 | 2/2010 | von Mueller et al. |
| 2010/0150465 | A1 | 6/2010 | Lee et al. |
| 2010/0244818 | A1 | 9/2010 | Atwood et al. |
| 2010/0327856 | A1 | 12/2010 | Lowy |
| 2011/0031985 | A1 | 2/2011 | Johnson |
| 2011/0048756 | A1 | 3/2011 | Shi et al. |
| 2011/0090658 | A1 | 4/2011 | Adams et al. |
| 2011/0135092 | A1 | 6/2011 | Lehner |
| 2011/0253788 | A1 | 10/2011 | Campbell et al. |
| 2012/0002313 | A1 | 1/2012 | Miyabe et al. |
| 2012/0047374 | A1 | 2/2012 | Klum et al. |
| 2012/0091201 | A1 | 4/2012 | Babu et al. |
| 2012/0151607 | A1* | 6/2012 | Chambourov ......... H01H 13/79 726/34 |
| 2012/0163434 | A1 | 6/2012 | Kim et al. |
| 2012/0286760 | A1 | 11/2012 | Carapelli et al. |
| 2013/0055416 | A1 | 2/2013 | Ma et al. |
| 2013/0104252 | A1 | 4/2013 | Yanamadala et al. |
| 2013/0111227 | A1 | 5/2013 | Sauerwein, Jr. |
| 2014/0002239 | A1 | 1/2014 | Rayner |
| 2014/0049887 | A1 | 2/2014 | Salle |
| 2014/0070006 | A1 | 3/2014 | Weldele et al. |
| 2014/0081874 | A1 | 3/2014 | Lewis et al. |
| 2014/0124576 | A1 | 5/2014 | Zhou et al. |
| 2014/0204529 | A1 | 7/2014 | White et al. |
| 2014/0211336 | A1 | 7/2014 | Liao et al. |
| 2015/0097572 | A1* | 4/2015 | Wade ..................... G06K 7/0095 324/537 |
| 2015/0224892 | A1 | 8/2015 | Callicoat et al. |
| 2017/0104325 | A1* | 4/2017 | Eriksen ................... H02H 3/00 |
| 2017/0324195 | A1* | 11/2017 | Eriksen ................... H02H 3/00 |

FOREIGN PATENT DOCUMENTS

| | | | |
|---|---|---|---|
| DE | 103 40 289 A1 | | 3/2005 |
| KR | 10-2008-0105500 A | | 12/2008 |
| WO | 2004/086202 A1 | | 10/2004 |
| WO | 2015/050746 A1 | | 4/2015 |

OTHER PUBLICATIONS

Non-Final Office Action dated Feb. 24, 2015 for U.S. Appl. No. 14/296,310, of Wade, J., et al. filed Jun. 4, 2014.
Notice of Allowance dated Jul. 29, 2015 for U.S. Appl. No. 14/296,310, of Wade, J., et al. filed Jun. 4, 2014.
Non-Final Office Action dated Nov. 13, 2015, for U.S. Appl. No. 14/046,791, of Wade, J., et al., filed Oct. 4, 2013.
Non Final Office Action dated Dec. 31, 2015, for U.S. Appl. No. 14/285,438, of Wade, J., filed May 22, 2014.
Notice of Allowance dated Jan. 20, 2016, for U.S. Appl. No. 14/046,791, of Wade, J., et al., filed Oct. 4, 2013.
Non-Final Office Action dated Jan. 25, 2016 for U.S. Appl. No. 14/927,284, of Wade, J., et al. filed Oct. 29, 2015.
Notice of Allowance dated May 31, 2016 for U.S. Appl. No. 14/927,284, of Wade, J., et al. filed Oct. 29, 2015.
Final Office Action dated Jun. 6, 2016, for U.S. Appl. No. 141285,438, of Wade, J., filed May 22, 2014.
Advisory Action dated Aug. 18, 2016, for U.S. Appl. No. 14/285,438, of Wade, J., filed May 22, 2014.
Notice of Allowance dated Oct. 25, 2016, for U.S. Appl. No. 14/285,438, of Wade, J., filed May 22, 2014.
Non Final office Action dated Dec. 6, 2016, for U.S. Appl. No. 15/224,450, of Wade, J., et al. filed Jul. 29, 2016.
First Examination Report for Australian Patent Application No. 2014329851, dated Dec. 15, 2016.
Non Final Office Action dated Jan. 20, 2017, for U.S. Appl. No. 14/184,636, of Wade, J., et al., filed Feb. 19, 2014.
Notice of Acceptance for Australian Patent Application No. 2014329851, dated Mar. 6, 2017.
Final office Action dated May 8, 2017, for U.S. Appl. No. 15/224,450, of Wade, J., et al. filed Jul. 29, 2016.
Final Office Action dated Aug. 2, 2017, for U.S. Appl. No. 14/184,636, of Wade, J., et al., filed Feb. 19, 2014.
Notice of Allowance dated Aug. 24, 2017, for U.S. Appl. No. 15/224,450, of Wade, J., et al. filed Jul. 29, 2016.
Advisory Action dated Oct. 26, 2017, for U.S. Appl. No. 14/184,636, of Wade, J., et al., filed Feb. 19, 2014.
Non Final office Action dated Feb. 23, 2018, for U.S. Appl. No. 15/250,460, of Razaghi, M., filed Aug. 29, 2016.
Non Final Office Action dated May 11, 2018, for U.S. Appl. No. 15/250,468, of Razaghi, M., filed Aug. 29, 2016.
International Search Report and Written Opinion for International Application No. PCT/US2014/057044, dated Dec. 19, 2014.

(56) References Cited

OTHER PUBLICATIONS

Extended European Search Report for European Patent Application No. 14850478.0, dated May 16, 2017.
Non-Final Office Action dated Dec. 29, 2016, for U.S. Appl. No. 15/250,446, of Razaghi, M., filed Aug. 29, 2016.
Notice of Allowance dated Apr. 13, 2017, for U.S. Appl. No. 15/250,446, of Razaghi, M., filed Aug. 29, 2016.
Office Action for European Patent Application No. 14 850 478.0, dated Aug. 30, 2018.
Notice of Allowance dated Sep. 13, 2018, for U.S. Appl. No. 15/250,468, of Razaghi, M., filed Aug. 29, 2016.
Non Final Office Action dated Oct. 5, 2018, for U.S. Appl. No. 14/184,636, of Wade, J., et al., filed Feb. 19, 2014.
Notice of Allowance dated Dec. 3, 2018, for U.S. Appl. No. 15/250,460, of Razaghi, M., filed Aug. 29, 2016.
Corrected Notice of Allowance dated Dec. 28, 2018, for U.S. Appl. No. 15/250,468, of Razaghi, M., filed Aug. 29, 2016.
Final Office Action dated May 23, 2019, for U.S. Appl. No. 14/184,636, of Wade, J., et al., filed Feb. 19, 2014.
Notice of Allowance dated Jul. 19, 2019, for U.S. Appl. No. 15/581,871 of Hafemann, S., et al. filed Apr. 28, 2017.
Advisory Action dated Jul. 23, 2019, for U.S. Appl. No. 14/184,636, of Wade, J., et al., filed Feb. 19, 2014.

* cited by examiner

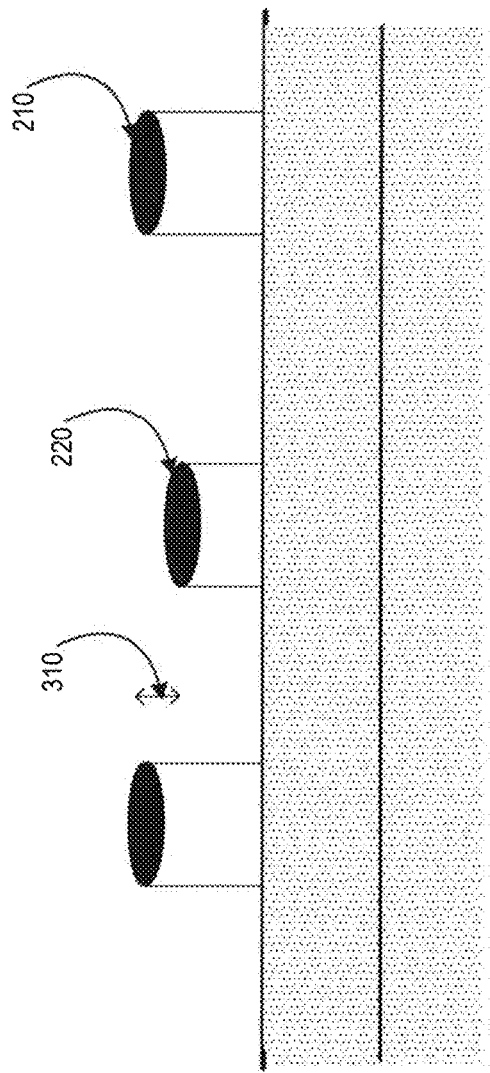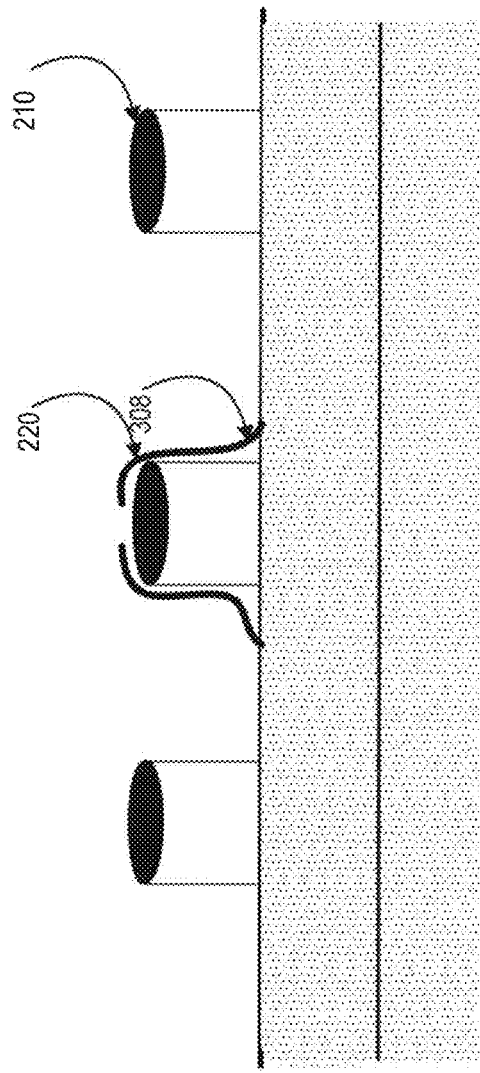

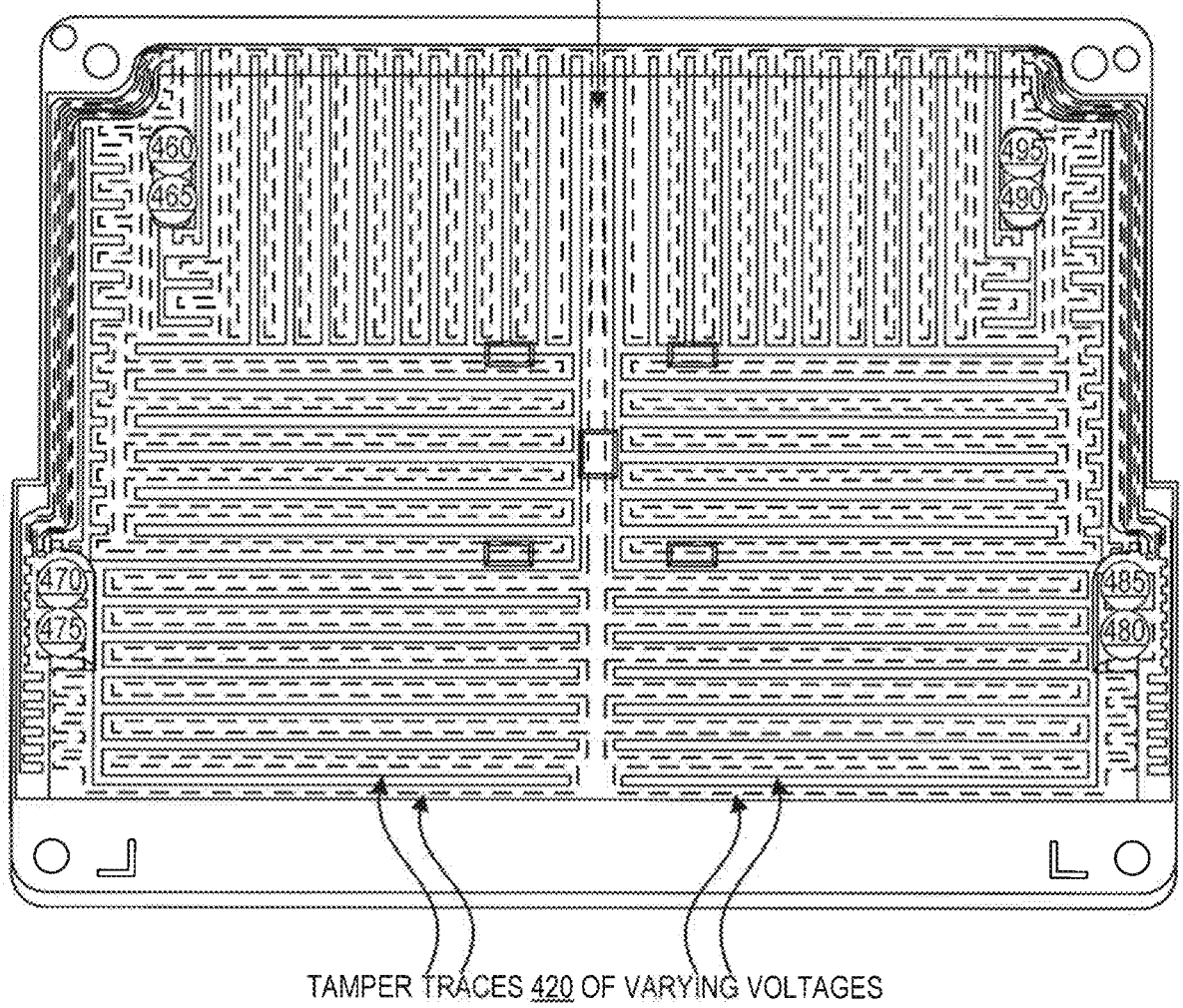

TAMPER DETECTION SYSTEM

BACKGROUND

Electronic payments may be performed in a variety of ways. A payment terminal may process payment transactions, and may interact with payment devices such as a payment card having a magnetic strip that is swiped in a magnetic reader of the payment terminal, a payment device having a Europay/Mastercard/Visa (EMV) chip that is dipped into corresponding EMV slot of the payment terminal, and near field communication (NFC) enabled devices such as a smartphone or EMV card that is tapped to the payment terminal and transmits payment information over a secure wireless connection. The payment terminal may receive payment information from the payment device as well information about a transaction, and may communicate this information to a payment system for processing of the transaction.

As of a result of its central role in the transaction processing system, the payment terminal is a prime target for third party attackers attempting to access payment information, process fraudulent transactions, and otherwise engage in fraudulent activities or theft. In many cases, the attackers attempt to physically access components of the payment terminal, such as one or more communication lines carrying data or a processor that communicates and processes payment information. Attackers may attempt to eavesdrop on signals (e.g., a passive attack) or to modify or spoof payment processing communications (e.g., an active attack) by injecting malicious signals into the payment terminal.

In an effort to thwart physical attacks, payment terminals may implement tamper detection devices such tamper meshes and tamper switches. For example, if an attacker attempts to remove the cover of the payment terminal, a tamper switch may open. A tamper mesh may include a conductive trace that effectively covers sensitive components such as the processor or other circuitry of the payment terminal. If an attacker attempts to access the sensitive components (e.g., by drilling a small hole into the payment terminal), the conductive trace may be broken, resulting in an open circuit. The open circuit of the tamper switch or tamper mesh may be sensed by circuitry of the payment terminal, which may shut off the payment terminal or take other corrective action.

BRIEF DESCRIPTION OF THE DRAWINGS

The above and other features of the present disclosure, its nature and various advantages will be more apparent upon consideration of the following detailed description, taken in conjunction with the accompanying drawings in which:

FIG. 3B illustrates a side view of a sub-flush guard ring assembly in a tamper detection system, according to another embodiment of the present subject matter FIG. 3C illustrates a side view of a sub-flush guard ring assembly in a tamper detection system, according to yet another embodiment of the present subject matter.

FIG. 4C illustrates the interior surface of the top housing with an exemplary arrangement of tamper traces of varying voltages.

Figure 1A:
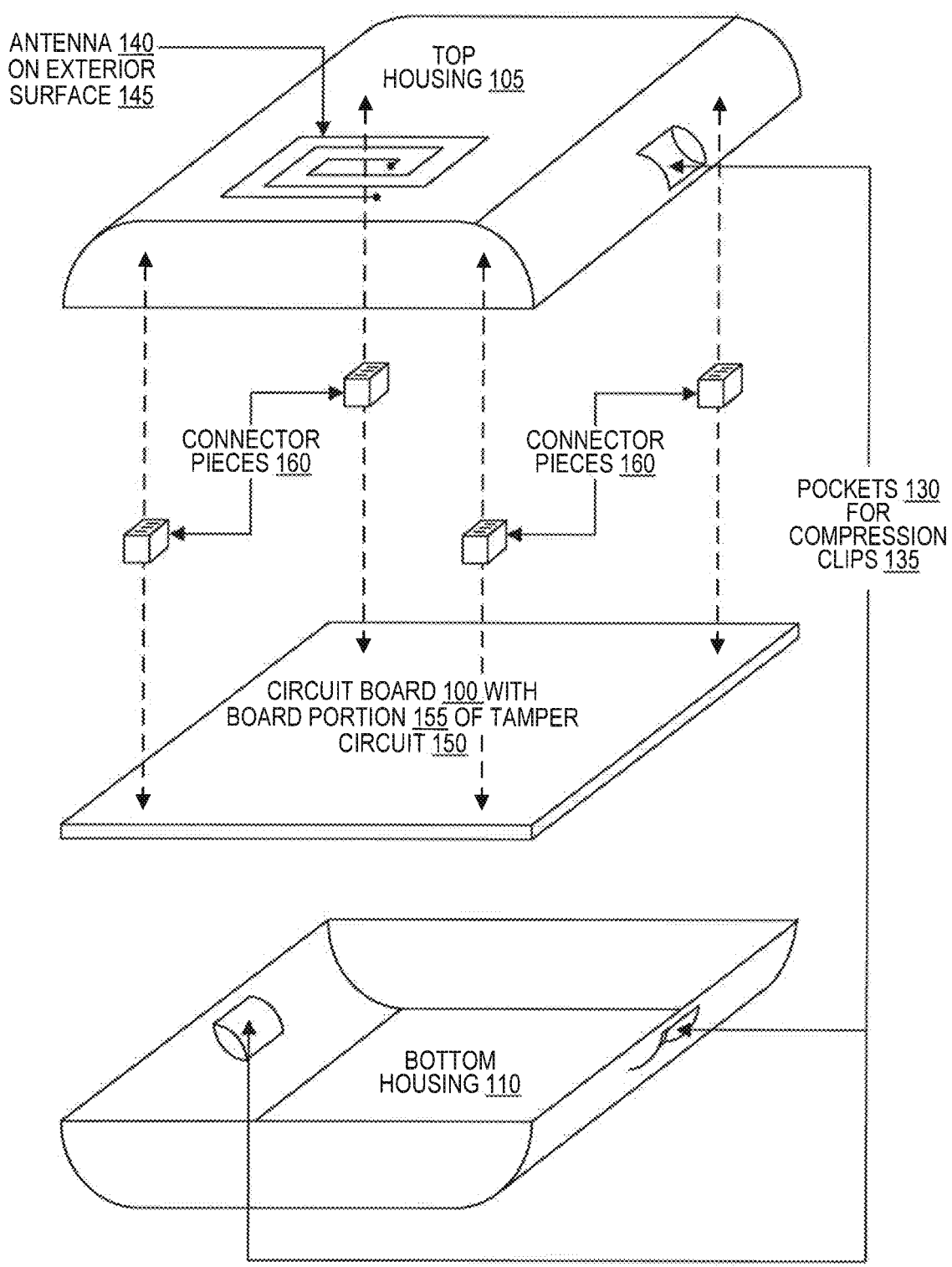
FIG. 1A is an exploded perspective view of a circuit board enclosed within a top housing and a bottom housing and connected to the top housing via connector pieces.

In the figures, the left-most digit(s) of a reference number identifies the figure in which the reference number first appears. The use of the same reference numbers in different figures indicates similar or identical items or features. Moreover, multiple instances of the same part are designated by a common prefix separated from the instance number by a dash. The drawings are not to scale.

DETAILED DESCRIPTION

An electronic payment terminal such as a payment reader may interface with various types of payment devices. For example, smart phones and smart watches have NFC payment applications that allow a customer to "tap" in close proximity to the payment terminal in order to pay. Payment information is transmitted and received wirelessly over a radio frequency (RF) connection between the payment device and the payment reader. EMV cards include an EMV chip that is "dipped" into a slot in the payment reader. The EMV card typically remains in the reader, and communicates with the payment reader through a physical electrical connection. Once the transaction is complete, the EMV card may be removed. Also, many payment cards retain traditional "swipe" technology in which information about a payment card is transferred to the payment reader by swiping a magnetic card stripe through a magnetic reader of the payment reader.

In all of these scenarios, there are multiple opportunities for an attacker to attempt to obtain the payment information in order to steal payment data or otherwise engage in fraudulent transactions. For example, an attacker may attempt to intercept NFC communications, read data being communicated over the physical connections with the EMV card, or intercept that data from the magnetic stripe of a traditional swiping transaction. Moreover, signals carrying this and other critical information are transmitted within the payment reader and processed by processors and other circuitry of the payment reader.

Accordingly, numerous types of tamper detection devices such as tamper switches and tamper meshes are integrated into an exemplary payment reader. These tamper detection devices can sense attempts to gain improper physical access to the payment reader (e.g., by opening the payment reader or drilling into the payment reader to access signals or components), attempts to physically provide electrical signals to the payment reader (e.g., attempts to inject malicious signals into externally accessible pins of the payment reader, such as EMV pins), and attempts to wirelessly introduce malicious signals to the payment reader. Some tamper detection devices may open a circuit in response to tamper attempt.

The payment reader includes tamper detection circuitry for interacting with and controlling the various types of tamper detection devices. One such tamper detection method and system operates on conductive traces such that any substantial voltage variation on the trace, for example through interference with the trace or an actual open circuit, is indicative of a tamper event. In some embodiments, the conductive trace can include a wire mesh, which can be disposed along a circuit board layer within the electronic device. The term "mesh" as used here refers to one or more conductive traces that may be, but are not necessarily, electrically coupled to each other. In some embodiments, the conductive trace can be interwoven with one or more other conductive traces. In particular, the different interwoven conductive traces can run very closely together, along spatially parallel paths, across one or more circuit board layers, to render it more difficult for an attacker to circumvent the traces of the electronic device. The mesh substantially covers the regions of the substrate for which protection is desired. It is preferred that the traces do not possess any long range order, i.e. it is preferred that the traces do not have a repeating pattern. The absence of such order increases security by minimizing the possibility of predicting the location of the traces. The mesh may be present between or within layers of components of the secure data entry device. For example, the substrate that contains the electronic circuitry, e.g. the PCB, may be formed from a plurality of layers and the mesh, particularly in the form of conductive traces, may be formed on or within one or more of these layers. This provides further protection by registering any tampering event that disrupts a conductive trace.

In some embodiments, the conductive trace can include a metal dome switch, which can be affixed to an electronic surface of a component of the electronic device (e.g., circuit board) during the manufacturing process. In such embodiments, the conductive trace (connected to the internal power supply) can be used to detect a short-circuit condition on the metal dome switch, such as may result from physical tampering. In some embodiments, the conductive trace can be combined with another conductive trace to facilitate detection of physical tampering with an input interface of the electronic device. In such embodiments, one trace can be disposed within a flexible circuit region of the input interface while the other trace is disposed spatially in parallel with the electrical connector between the input interface and the electronic device. Tampering is determined to be detected upon detection of a short-circuit condition on either trace.

Going back to dome switches, the dome switch can be affixed to an interior surface of the housing. The metal dome switch, which can be any conventional switch contact used to produce a positive tactile feedback, may be used to detect tampering through detection of an "un-depressed" physical state of the switch caused by an opening of the housing. The metal dome switch can include one or more conductive, overlapping rings that form a dome. In operation, the metal dome switch functions as a closed switch when it is depressed (e.g., pushed downward between two surfaces), and an open switch when un-depressed.

A conventional technique for tamper detection using a conventional metal dome switch is to affix the switch within an electronic device in a permanently depressed state. During the manufacturing process, for example, the metal dome switch can be depressed between a top ring that is affixed to an interior surface of a housing of the electronic device, and a bottom ring that is affixed to an electrical component or surface of the electronic device (e.g., circuit board). The metal dome switch would be intended to remain with its flexible (compressible) contact in the depressed state, in a closed switch condition, through the lifetime of the electronic device. Any unauthorized attempt to open the housing of the electronic device would remove the pressure that maintains the compression on the flexible contact of the switch. Such pressure removal would cause the metal dome switch to become an open switch condition, which can be detected as tampering (by, e.g., tamper detector).

A known form of attack on this conventional technique is to drill into the housing and inject conductive ink into the space between the top and bottom rings of the metal dome switch. With the conductive ink, the metal dome switch remains electrically in a closed switch condition regardless of the compression state of its flexible contact.

To counter the above-mentioned shortcomings of the conventional tamper detection technique, a third ring can be added to the traditional metal dome switch. So, the metal dome switch has a top ring, a middle ring, and a bottom ring, where the top ring and the bottom ring are the flexible contacts and the middle ring can be substantially like the inner and outer security rings and may substantially or entirely surround (e.g. concentrically) the inner and outer security rings. The top ring is connected to the tamper detector, the middle ring is connected to the trace, and the bottom ring is tied to ground. The middle ring is also referred to as guard ring throughout the description.

In operation, the tamper detection system having guard rings can detect tampering within the electronic device by detecting a tampering event on the metal dome switch. In one embodiment, the system detects tampering when there exists a short-circuit condition on the metal dome switch. Under normal operation, the guard ring, which is connected to the trace, and the bottom ring, which is grounded, are not in electrical contact with each other. If the guard ring becomes electrically connected to the bottom ring (e.g., as a result of conductive ink injected into the metal dome switch), a short-circuit condition will result. The guard ring may also form a physical barrier to prevent the malicious application of a conductive liquid or conductive member into the electronic device.

The system will detect such a short-circuit condition, where the collapse indicates tampering and in one of the schemes, following a tampering event, all key information is automatically erased to prevent it from getting in unauthorized hands. The guard ring, the top ring and the bottom ring ideally are generally attached to the dome or a housing of the device in an M-shaped configuration. The traditional way of creating such a structure is to have the rings fabricated on the same plane and have contacts of the dome switch connected to the contacts of the rings in an M-shaped configuration or convex configuration and as such extending away from the circuitry. However, due to the ever-shrinking form factor considerations and constraints, especially in the field of smaller form factor devices like portable payment readers, the M-shaped configuration is more realistically and non-ideally a flat-configuration causing the guard ring and the other two rings to be substantially in one plane.

As contemplated by the present subject matter, various actions, such as accidentally dropping the electronic device, or changes in environment, have been known to cause guard ring to potentially become electrically connected to the top or bottom ring due to the form factor constraints mentioned above. For example, if the device is in a high-temperature or high humidity environment, the guard ring, being substantially in the same plane as the other two rings, accidentally connects with one of the other rings (even it if for few nanoseconds) causing the tamper detection system to detect it has an open circuit and subsequently causing keys to be erased. False tampering positives like these cause sensitive and critical data to be deleted for no reason, which in turn can frustrate the user of the device.

To prevent at least the problems mentioned above, the present subject matter discloses an arrangement, fabrication and construction of guard ring, the top ring and the bottom ring to be in different planes or the same plane but for the guard ring to be of a width different from the bottom or top ring, or in some cases, the guard ring is sub-flushed with respect to the other rings. Thus, the implementation involves creating a guard ring to have a different physical configuration than the inner or outer ring. In one implementation, the guard ring is placed in a substrate layer different from the layer in which the top ring and bottom ring are placed. In another implementation, the fabrication process involves selectively applying a layer of solder mask on the guard ring, of width or thickness substantially between about 8 and about 10 microns. The guard ring can be fabricated as an embedded component, for example in a cavity, such that the length between the top or bottom ring and the guard ring is approximately 80 microns. The guard ring may be concentric and can be closer to the inner ring than the outer ring and vice versa. While the rings are shown to be circular, it will be understood that any shape and form is possible. Furthermore, certain fabrication techniques are discussed in the present subject matter, such as laser techniques or masking, however, these are not limiting and any technique that facilitates longitudinal gap between the inner and outer ring and the guard ring can be used. Also, while the guard ring is shown to be in second layer, or one layer lower than the inner and outer ring, the guard ring can be embedded in any layer and the size, such as width or height, can be smaller or bigger depending on the application.

In some applications, the guard ring can be fabricated with a thickness different from the inner and outer ring and in different layers. Furthermore, even though the guard ring is shown to be between the inner and outer ring, it will be understood that in some implementations, the guard ring can be outside the inner and outer rings. In some implementations, the guard ring can have a staggered structure having plurality of widths and heights for to detect varying levels of accidental tampering.

In some implementations, the guard ring and its fabrication follows a subtractive process. However, additive processes where substrate material can be added to create a guard ring of desired height and width.

FIG. 1A is an exploded perspective view of a circuit board enclosed within a top housing and a bottom housing and connected to the top housing via connector pieces. The exploded view of FIG. 1A illustrates a circuit board 100 protected by a security housing made up of a top housing 105 and a bottom housing 110. The circuit board 100 can read, store, and/or transmit sensitive information. For example, the circuit board 100 can store symmetric or asymmetric encryption keys for encrypting information transmitted to other circuitry not protected by the security housing, and can perform encryption and/or decryption operations using the encryption keys. The circuit board 100 can also include, or can be electrically connected to, one or more card reader components (not pictured) for reading transaction information stored by a transaction card such as a credit card, a debit card, an Automated Teller Machine (ATM) card, a store gift card, a public transit card, a driver's license, a personal identification card, a door entry card, a security badge, or some combination thereof. The circuit board 100 can also include, or can be electrically connected to, one or more computing interface components (not pictured) to receive transaction information from a portable computing device, such as a cellular phone or a portable media player with a wireless transaction capability through Near-Field-Communication (NFC) signals, radio-frequency identification (RFID) signals, BLUETOOTH™ wireless signals, or some combination thereof. The circuit board 100 can include non-transitory data storage media for temporarily or permanently storing such transaction information, as well as wired or wireless data-transfer means, such as cables, plugs, ports, or antennae, for transferring such data. The circuit board 100 can be single-sided or double-sided, and can be a printed circuit board (PCB), a printed wiring board (PWB) with non-printed components, a perfboard, a stripboard, a breadboard, or some combination thereof.

The circuit board 100 of FIG. 1A includes board portion 155 of a tamper detection circuit 150. The tamper detection circuit 150 may include various substrate layers, where one layer houses an inner ring and an outer ring, while a second layer, houses a guard ring. The board portion 155 of a tamper detection circuit 150, which on its own, is an incomplete circuit. When completed, the tamper detection circuit 150 conducts electricity across conductive tamper traces 420 (not shown in FIG. 1A) that snake around an interior surface of the security housing. One exemplary layout of the tamper traces 420 is illustrated in FIG. 4C. The tamper traces 420 can be connected to the board portion 155 of the tamper detection circuit 150 in such a way that some of the tamper traces 420 conduct different voltages than other tamper traces 420. The board portion 155 of the tamper detection circuit 150 includes monitor nodes (not shown in FIG. 1A) that monitor voltages at different points and can thus detect if current stops flowing across one or more tamper traces 420, or a short circuit is experienced among the tamper traces 420, issues that can occur if a malicious party tampers with the security housing by drilling into the security housing, by attempting to reroute current within the tamper detection circuit 150, or by flooding a portion of the tamper detection circuit 150 with conductive ink. The tamper detection circuit 150, when completed, can be arranged in a discrete comparison circuit layout or can be arranged in a wheat-stone bridge layout (not shown). The discrete comparison circuit layout can, in certain environmental conditions such as high heat or high humidity, suffer from "false positive" reports of tampering when no actual tampering has occurred due to development a parasitic resistance between points of the tamper detection circuit 150 that are not directly connected. The wheat-stone bridge layout solves this issue.

The board portion 155 of the tamper detection circuit 150 is connected to the conductive tamper traces 420 of the security housing via connector pieces 160. Each connector piece can be at least partially elastic to ensure that the connection between the board portion 155 of the tamper detection circuit 150 and the conductive tamper traces 420 of the security housing do not disconnect during ordinary operations. Each connector piece 160 can be held in place by a board connector piece holder 255 as illustrated, for example, in FIG. 2B. The board portion 155 of the tamper detection circuit 150 can further be configured to detect tampering with the connector pieces 160 by detecting voltage changes caused by connections between the connector pieces 160 and various conductive elements (such as guard rings 220, inner and outer rings shown as connection nodes 210 or conductive board piece holders 255) placed around or near the connector pieces 160 that conduct different voltages than are flowing through the connector pieces themselves, such as the conductive guard rings 220 illustrated in FIG. 2A or the conductive board connector piece holders 255 illustrated in FIG. 2B, respectively.

While the exploded view of FIG. 1A illustrates both a top housing 105 and a bottom housing 110, some security housings can include only a top housing 105 or only a bottom housing 110. In embodiment with both a top housing 105 and a bottom housing 110, tamper traces 420 can run along the interior surfaces of both the top housing 105 and the bottom housing 110, or they can run along only one of the top housing 105 or the bottom housing 110. Tamper traces 420 of the top housing 105 can connect to tamper traces 420 of the bottom housing 110 or can remain separate.

Furthermore, while the top housing 105 and bottom housing 110 appear similarly shaped in FIG. 1A, this need not be the case; for example, the bottom housing 110 can be substantially flat while the top housing 105 can leave more room for components of the circuit board 100. Such an asymmetric layout can be used, for example, if the circuit board 100 is one-sided.

While the exploded view of FIG. 1A illustrates four connector pieces 160, it should be understood that in different embodiments, a different number of connector pieces 160 can be used to connect the circuit board 100 to the tamper traces 420. Likewise, while the exploded view of FIG. 1A only illustrates connector pieces 160 between the circuit board 100 and the top housing 105, in other embodiments, connector pieces 160 can be used to between the circuit board 100 and the bottom housing 110 as well.

The top housing 105 of FIG. 1A, optionally, includes an antenna 140 on the exterior surface 145 of the top housing 105. The antenna 140 can be a wireless receiver antenna, a wireless transmitter antenna, or a wireless transceiver antenna. The antenna 140 can be, for example, a cellular network antenna, a Bluetooth™ local wireless connection antenna, a Bluetooth™ Low Energy (BLE) local wireless connection antenna, a radio-frequency antenna, a microwave-frequency antenna, a television-frequency antenna, a near-field-communication (NFC) antenna, an IEEE 802.11 Wi-Fi wireless antenna, or some combination thereof. While the antenna 140 of FIG. 1A is positioned along an exterior surface 145 of the top housing 105, it can alternately be included into the non-conductive interior of top housing, or can alternately be positioned along an interior surface of the top housing 105. The antenna 140 can alternately be placed along or inside the bottom housing 105.

The non-conductive portions of the top housing 105 and bottom housing 110 can be made from plastic, such as thermoplastics manufactured using Laser Direct Structuring (LDS), or from other non-conductive materials. The non-conductive portions of the top housing 105 and bottom housing 110 can be fused to each other and/or to the non-conductive board of the circuit board 100 to prevent opening the security housing, or can alternately be affixed with glue, cement, or other adhesives. The tamper traces 420 can be laid out over inside surface of the security housing during an LDS manufacturing process, if it is used.

The top housing 105 and bottom housing 110 of FIG. 1A also illustrates several pockets 130 to receive compression clips 135. The compression clips 135 function not only to keep the security housing fastened to the circuit board 100, but also to prevent bowing in the non-conductive board 200 portion of the circuit board 100 itself, a common issue that can affect circuit boards 100 over time and eventually cause damage circuitry. The compression clips 135 themselves are not pictured in FIG. 1A, but can be any type of clips that provide pressure, such as clips based on elastomers, clips based on springs, clips based on metals with elastic properties, magnetic clips, or some combination thereof. The compression clips 135 can alternately be clamps, such as manually closed screw-based clamps.

The one or more reader components of the circuit board 100 can include a magnetic read head or other type of magnetic stripe reader that is capable of reading information from a magnetic stripe of a transaction card. The one or more reader components can also include an integrated circuit (IC) chip reader for reading an IC chip embedded in a transaction card. Such an IC chip can follow the Europay-Mastercard-Visa (EMV) payment IC chip standard. The IC chip reader can be contact-based, in that it can include one or more conductive prongs that contact a conductive metal contact pad of the IC chip. The IC chip can instead be contactless and use a contactless antenna. The contactless antenna can also double as a receiver for near-field-communication (NFC) signals, radio-frequency identification (RFID) signals, BLUETOOTH™ wireless signals, or some combination thereof, which can be sent from a transaction card or from a portable computing device.

Figure 1B:
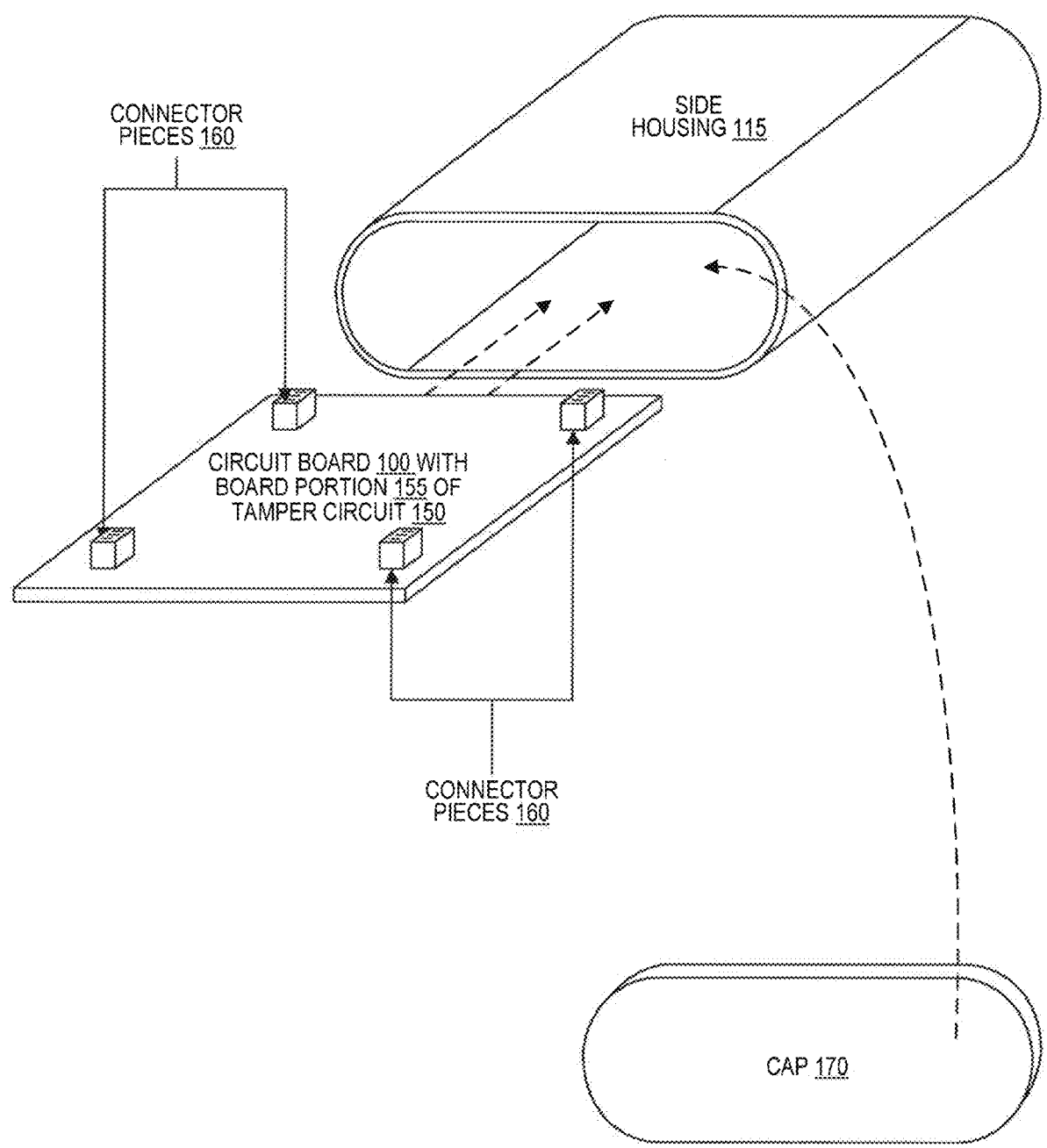
FIG. 1B is an exploded perspective view of a circuit board enclosed within a side housing and connected to the side housing via connector pieces.

FIG. 1B is an exploded perspective view of a circuit board enclosed within a side housing and connected to the side housing via connector pieces. The side housing 115 can receive the circuit board 100 and connector pieces 160 through a side opening, after which a cap 170 can be fused or adhered to the side housing. The side housing 115 can include tamper traces 420 all along its interior. The cap 170 can likewise include tamper traces 420 along its interior surface. Any tamper traces 420 of the cap 170 can connect to tamper traces 420 of the side housing 115.

Another alternate embodiment of the security housing (not pictured) can include two smaller side housings 115 fused together, each enclosing a portion of the circuit board, including a "left-side" side housing and a "right-side" side housing, each with conductive tamper traces 420 running along its interior. Tamper traces 420 of the "left-side" side housing can connect to tamper traces 420 of the "right-side" side housing or can remain separate.

Figure 2A:
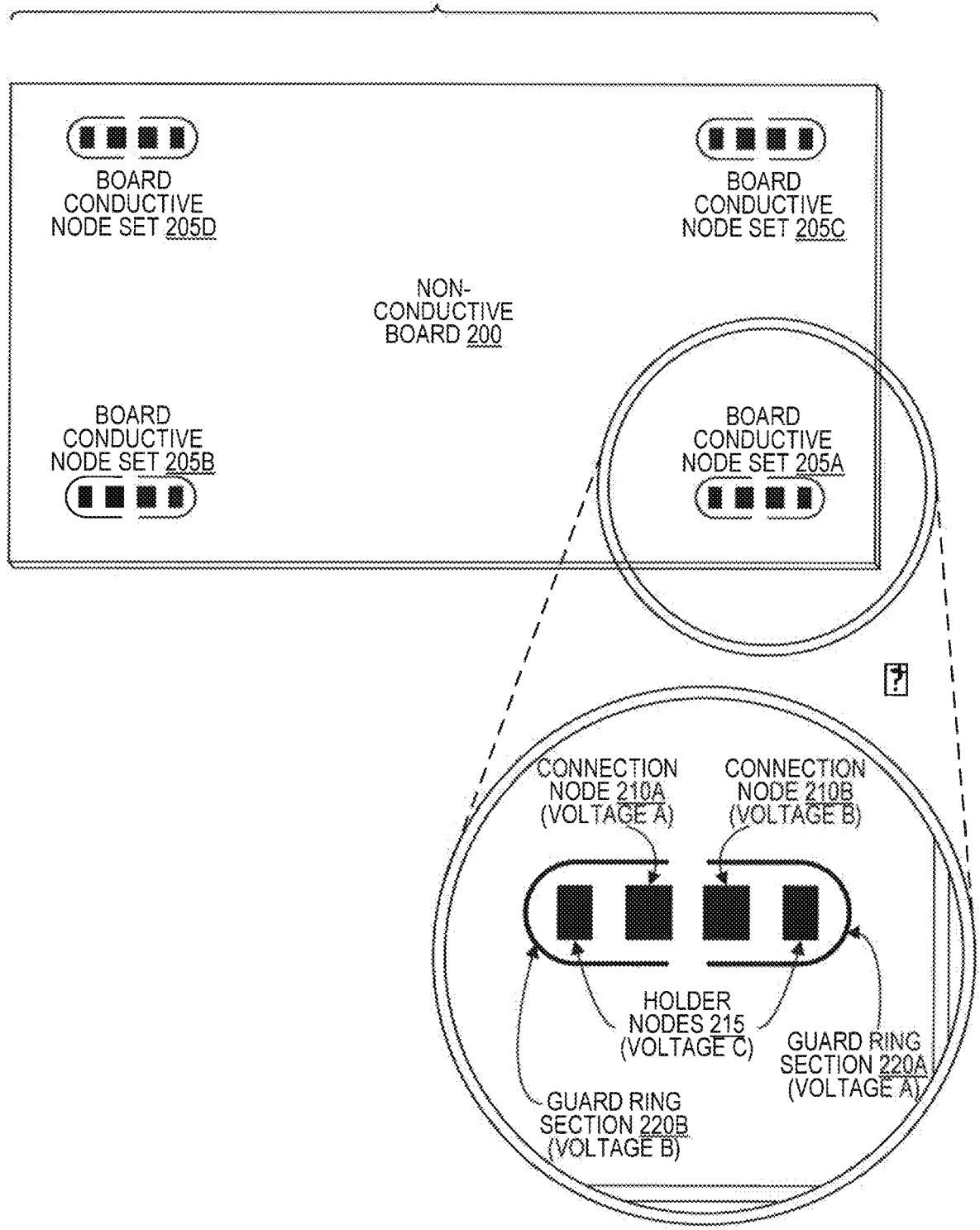
FIG. 2A illustrates a top-down view of a circuit board with four board conductive node sets, with a close-up view of one board conductive node set.

FIG. 2A illustrates a top-down view of a circuit board with four board conductive node sets, with a close-up view of one board conductive node set. The circuit board 100 of FIG. 2A includes a non-conductive board 200 with four board conductive node sets 205, identified by identifiers 205A, 205B, 205C, and 205D, respectively. While the four board conductive node sets 205 are spaced roughly evenly along the non-conductive board 200, they can alternately be place asymmetrically or clustered in a different layout.

The close-up view of FIG. 2A illustrates a close-up of board conductive node set 205A. The conductive node set 205A of FIG. 2A includes a first connection node 210A configured to conduct a first voltage A and a second connection node 210B configured to conduct a second voltage B. The first connection node 210A and the second connection node 210B are configured to be connected to the tamper traces 420 via a connector piece 160, and form part of the board portion 155 of the tamper detection circuit 150.

Figure 2B:
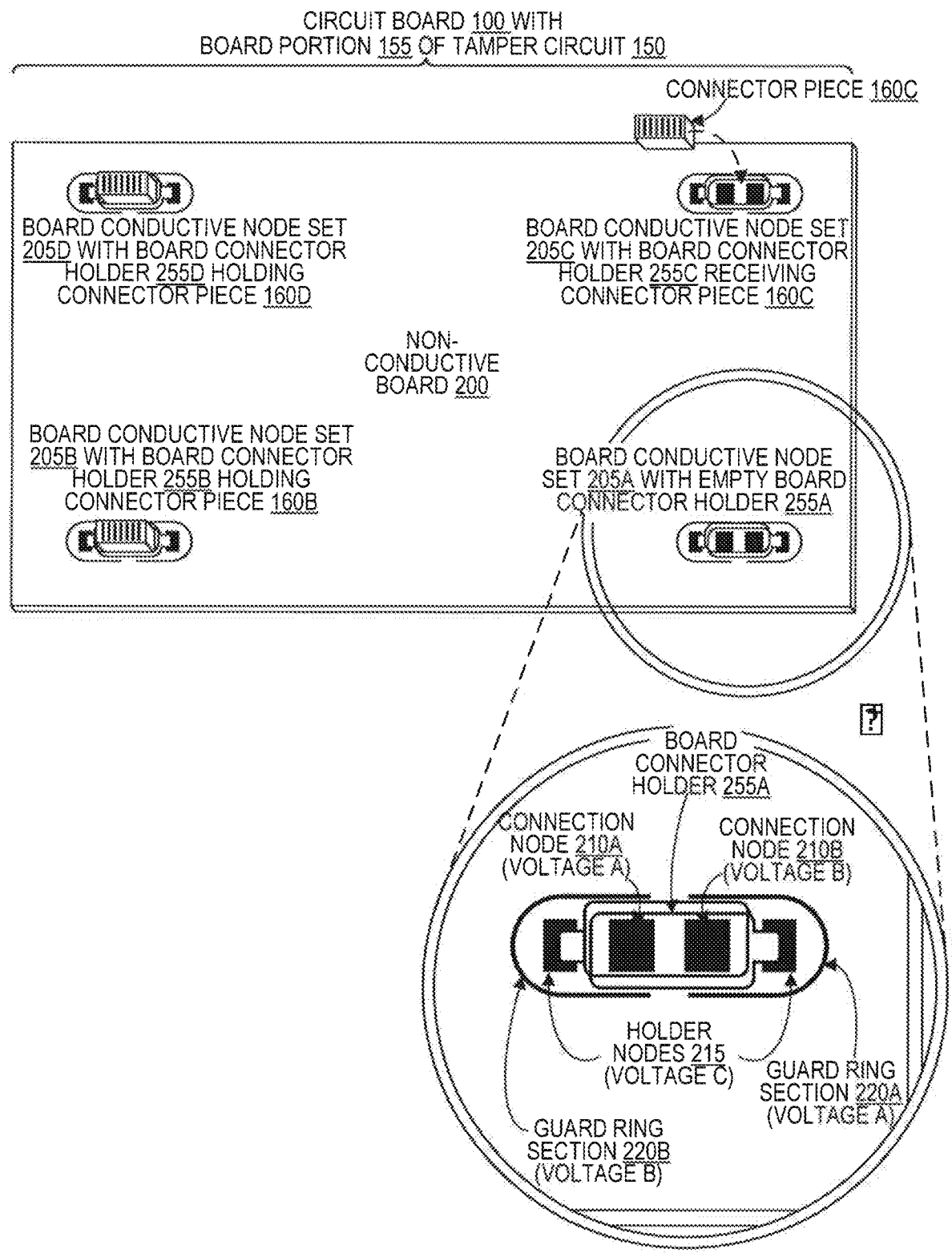
FIG. 2B illustrates a top-down view of a circuit board with four board conductive node sets, each attached to a board connector holder for holding a connector piece, with a close-up view of one board conductive node set and its attached board connector holder.

The conductive node set 205A of FIG. 2A also includes two holder nodes 215 configured to conduct a third voltage C. The holder nodes 215 can be connected to part of the board portion 155 of the tamper detection circuit 150. This can be, for example, a grounded part of the board portion 155 of the tamper detection circuit 150, in which case the voltage C can be zero. The holder nodes 215 can alternately be connected to a separate power supply, or connected directly to ground, in which case the voltage C can again be zero. The holder nodes 215 are optional and are configured to be electrically connected to conductive board connector holders 255 as illustrated in FIG. 2B. The holder nodes 215 can be omitted if non-conductive board connector holders 255 are used. If the holder nodes 215 are part of the board portion 155 of the tamper detection circuit 150, then removal of a board connector holders 255 would further be detectable at the monitor nodes 530 of the board portion 155 of the tamper detection circuit 150.

The conductive node set 205A of FIG. 2A also includes a guard ring 220. One or both guard ring sections 220 can be connected to parts of the board portion 155 of the tamper detection circuit 150. The guard ring of FIG. 2A includes two guard ring sections 220, namely a first guard ring section 220A configured to conduct the first voltage A and a second guard ring section 220B configured to conduct the second voltage B. The guard ring sections of FIG. 2A are positioned so that the first guard ring section 220A partially encircles the second connection node 210B, while the second guard ring section 220B partially encircles the first connection node 210A. In this way, each guard ring section 220 carries the opposite voltage as the connection node 210 that it partially encircles, meaning that a connection between the two would cause a short detectable at the monitor nodes 530 of the board portion 155 of the tamper detection circuit 150. Such a short could be caused; for example, by a malicious party flooding the board conductive node set 205A with conductive ink. In one implementation, the guard ring 220 is in a plane different from the conductive node set 205A or 205B, or the connection holder pieces 255A or 255B shown in FIG. 2B. Thus, in an event where there is an accidental dropping of the electronic device including the circuit board or a temperature related anomaly that causes a tampering event, the guard ring does not accidentally short with the conductive node set. This helps prevent a false tampering positive with the electronic device.

In an alternate embodiment, the one or both guard ring sections 220 can conduct a fourth voltage D, and can be connected to a separate power supply, or connected directly to ground, in which case the voltage D can be zero. In another alternate embodiment, the guard ring can be whole rather than divided into sections.

The circuit board 100 of FIG. 2A can include other components not pictured in FIG. 2A, such as components for reading, storing, or transmitting sensitive information as previously described in relation to FIG. 1A.

FIG. 2B illustrates a top-down view of a circuit board with four board conductive node sets, each attached to a board connector holder for holding a connector piece, with a close-up view of one board conductive node set and its attached board connector holder.

The circuit board 100 of FIG. 2B is the same circuit board 100 as the one illustrated in FIG. 2A, with the addition of four board connector holders 255. In particular, a first board connector holder 255A is illustrated over the first board conductive node set 255A, a second board connector holder 255B is illustrated over the second board conductive node set 255B, a third board connector holder 255C is illustrated over the third board conductive node set 255C, and a fourth board connector holder 255D is illustrated over the fourth board conductive node set 255D.

A second connector piece 160B is illustrated as held by the second board connector holder 255B, a third connector piece 160C is illustrated as held by the third board connector holder 255C, and a fourth connector piece 160D is illustrated as being placed into the fourth board connector holder 255D. While the first board connector holder 255A is illustrated as empty, with no corresponding first connector piece 160A, it should be understood that the first board connector holder 255A is also configured to hold a connector piece 160.

The close-up of the board conductive node set 250A of FIG. 2B is similar to the close-up of the board conductive node set 250A of FIG. 2A with the addition of the conductive board connector holder 255A. As discussed in relation to the close-up of FIG. 2A, the board connector holder 255A is electrically connected to the holder nodes 215, and therefore the board connector holder 255A itself conducts the voltage C.

Because the holder nodes 215 can be connected to the board portion 155 of the tamper detection circuit 150, the monitor nodes (not shown) of the board portion 155 of the tamper detection circuit 150 can detect disruption of the tamper detection circuit 150 from removal of the board connector holder 255. Furthermore, any damage to a board connector holder 255, such as damage from a malicious party drilling through a side of the security housing and through the board connector holder 255, can either sever the current running through the board connector holder 255 or can cause a short by connecting the board connector holder 255 to another element, such as the connector holder 160 enclosed within the board connector holder 255. Accordingly, use of the board connector holder 255 provides additional security.

The board connector holder 255 can be made of a metal or another conductive material, such as a carbon-based conductor. In addition to allowing the board connector holder 255 to conduct, the hardness of the material allows the board connector holder 255 to be thinner than a plastic connector holder. The hardness of the material also allows the board connector holder 255 to be constructed to include sidewalls that are perpendicular to the non-conductive board 200. Thus, use of board connector holders 255 allows the entire system—the circuit board 100 enclosed by the security housing—to be small in addition to being secure.

Figure 3A:
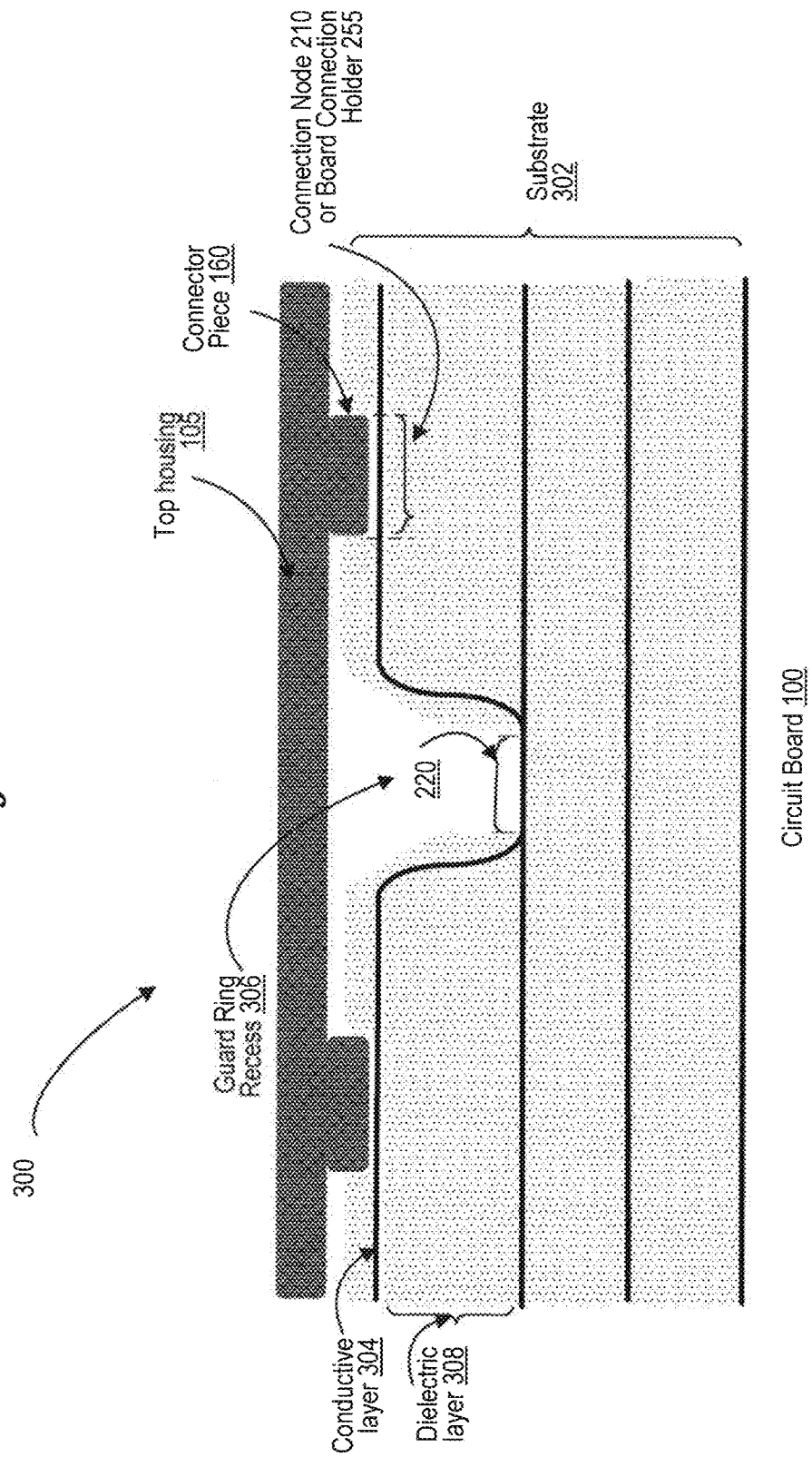
FIG. 3A illustrates a side view of a sub-flush guard ring assembly in a tamper detection system, according to an embodiment of the present subject matter.

FIG. 3A is an exploded side view of an exemplary guard ring assembly 300 shown to be embedded within a recessed cavity. The substrate 302 of the circuit board includes a number of layers, such as copper layers 304. Traditionally, the guard ring 220 and the connection nodes 210 (such as an inner ring and an outer ring) that connect to the housing, for example top housing 105 and its connector pieces 160, through board connection holders 255 or connection nodes 210, are in the same plane and are fabricated in the same copper layer 304. The connection nodes 210 can be replaced with board connector holder 255 or holder nodes 215, depending on the kind of implementation. As such, a first sensor element is the guard ring and the second sensor element is one of the connection nodes 210, the holder nodes 215 or the board connection holder 255. However, when such an assembly is connected to the housing, unintentional tampering activation can occur. Thus, to summarize, intentional tampering is caused by injecting conductive ink in a portion of the tamper detection circuit having the conductive tamper traces, and unintentional tampering is caused by accidentally dropping the secure electronic system or accidentally exposing the secure electronic system to temperature, pressure or humidity within an acceptable range defined by a model that computes an acceptable range of values that can occur in the field and are not a result of tampering techniques.

To counter such issues, the guard ring assembly is sub-flushed with respect to the connection nodes 210 as disclosed herein, and as such disposed or embedded in a cavity or trench with respect to the connection nodes 210. For this, the guard ring 220 is etched into the layer below the inner and outer ring and fabricated such that the guard ring has a height substantially smaller than the connection nodes 210. The guard ring 220 can also be in a layer much lower than the layer in which the conductive layers 304 are present, so for example, layer 3 or layer 4. The width of the trench can be more than the width of the conductive nodes (also referred to as inner and outer rings) since the guard ring is now in a different layer and within a guard ring recess 306. For this, the circuit board 100 includes a substrate 302 that further includes multiple conductive or copper layers 304 separated by dielectric layers 308. To form embedded components such as the guard ring 220, the holders or nodes 210 are fabricated in a conductive layer 304 different from guard ring's conductive layer 304.

An insulative coating similar to dielectric layer 308 is then laid on top of the recessed area other than over the guard ring 220. Thus, the implementation involves creating a guard ring to have a different physical configuration than the inner or outer ring, represented here by the connection nodes 210 or holder nodes 255. In one implementation, the guard ring is placed in a substrate layer different from the layer in which the top ring and bottom ring are placed. In another implementation, the fabrication process involves selectively applying a layer of solder mask on the guard ring, of width or thickness substantially between about 8 and about 10 microns. The guard ring 220 can be fabricated as an embedded component, for example in a cavity, such that the length between the top or bottom ring and the guard ring is approximately 80 microns. The guard ring may be concentric and can be closer to the inner ring than the outer ring and vice versa. While the rings are shown to be circular, it will be understood that any shape and form is possible. Furthermore, certain fabrication techniques are discussed in the present subject matter, such as laser techniques or masking, however, these are not limiting and any technique that facilitates longitudinal gap between the inner and outer ring and the guard ring can be used. Also, while the guard ring is shown to be in second layer, or one layer lower than the inner and outer ring, the guard ring can be embedded in any layer and the size, such as width or height, can be smaller or bigger depending on the application.

In some applications, the guard ring 220 can be fabricated with a thickness different from the inner and outer ring and in different layers. Furthermore, even though the guard ring is shown to be between the inner and outer ring, it will be understood that in some implementations, the guard ring can be outside the inner and outer rings.

Because the guard ring 220 in the recess 306 is within a trench, it is further away from the housing 105 and connector pieces 160, thus preventing accidental activation by coming into contact with the circuit board 100 and causing a short circuit or other unwanted connection. This protects both the tamper detection circuit 150 and the circuit board 100 from electrical interference.

Operationally, a first sensor element (such as a connection node) is disposed on a circuit board of the tamper detection circuit; a second sensor element (such as a connector piece 160) is disposed within an interior surface of a housing of the tamper detection circuit; and a guard ring 220 disposed on the circuit board of the tamper detection circuit configured to form an electrical connection with the first sensor element in response to injection of conductive fluid thereby indicating tampering with the tamper detection circuit, wherein the guard ring is configured to be on a plane substantially different from the first sensor element to prevent unintentional activation of the tamper detection circuit.

Structurally, to achieve this, in one implementation, a mechanical switch configured to indicate a non-tampered condition while closed and to indicate a tampered condition while open, the mechanical switch includes a fixed conductor located in a first plane of a circuit board; a mobile conductor configured to contact the fixed conductor while the mechanical switch is closed and further configured not to contact the fixed conductor while the mechanical switch is open; and a guard conductor configured to form an electrical connection with the fixed conductor or with the mobile conductor via a conductive fluid in response to injection of the conductive fluid into the mechanical switch, wherein the guard conductor is located in a second plane of the circuit board substantially different from the first plane to prevent a direct contact between the guard conductor and the fixed conductor or mobile conductor.

FIG. 3B is an exploded side view of an exemplary guard ring assembly shown to be in the same plane as connection nodes 210 but having a different height. The difference in depth is shown by arrow 310. In some implementations, the guard ring can have a staggered structure having plurality of widths and depths for to detect varying levels of accidental tampering.

FIG. 3C is an exploded side view of an exemplary guard ring assembly shown to be covered by an insulative side covering 308, which prevents unintentional activation of the tamper detection circuitry. A solder mask layer, for example, covers a portion of the conductive surface of the guard ring 220. A conductive land is shown with an opening in the solder mask layer 308.

Figure 4A:
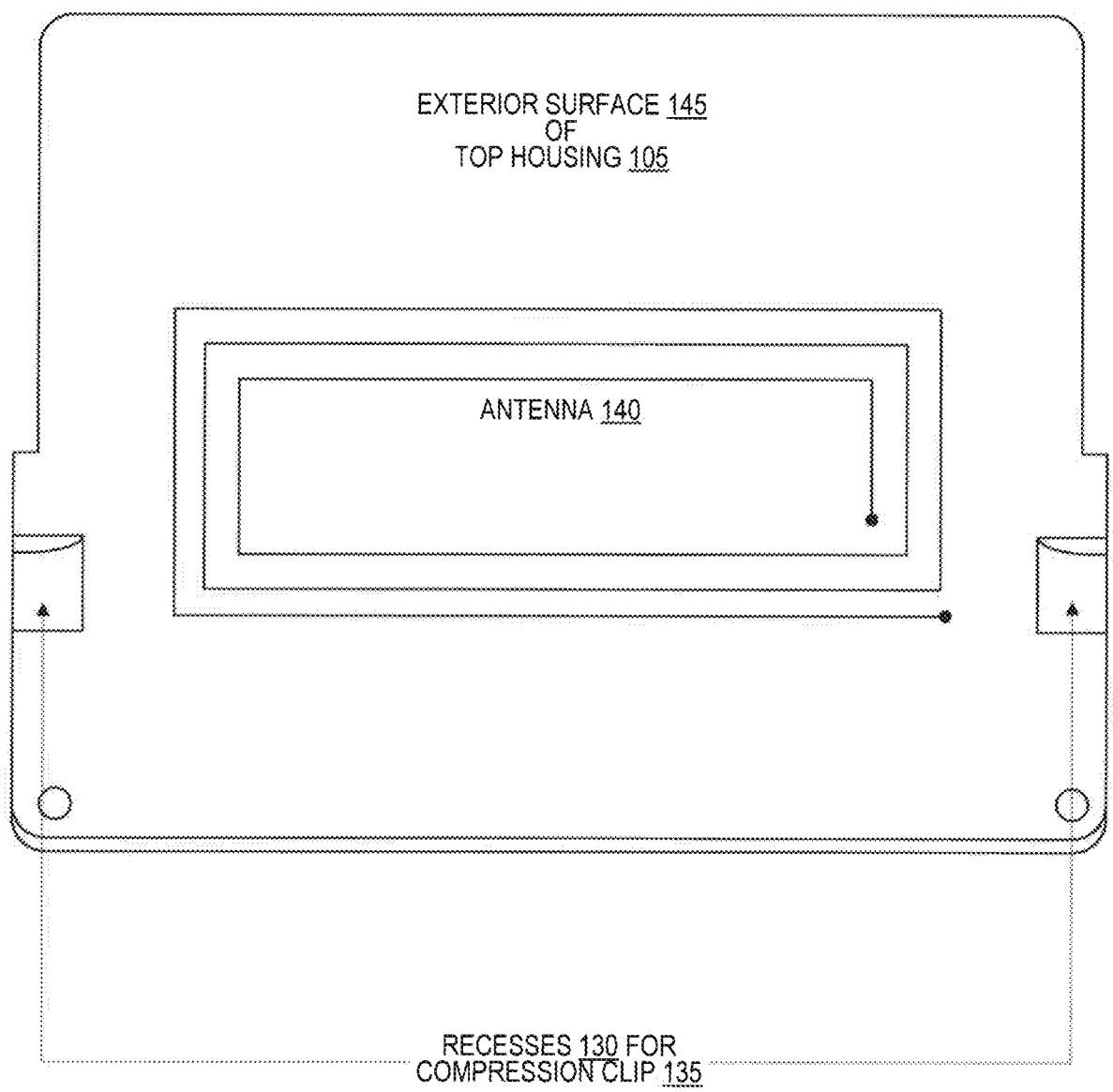
FIG. 4A illustrates an exterior surface of a top housing.

FIG. 4A illustrates an exterior surface of a top housing. The top housing 105 of FIG. 4A has a different shape than the top housing 105 illustrated in FIG. 1A. The top housing 105 of FIG. 4A also includes the antenna 140 along its exterior surface 145. The antenna 140 can be any type of antenna 140 discussed with respect to FIG. 1A. While the housing of FIGS. 4A, 4B, and 4C are labeled as a top housing 105, it should be understood that a bottom housing 110 or side housing 115 can be similarly structured.

Figure 4B:
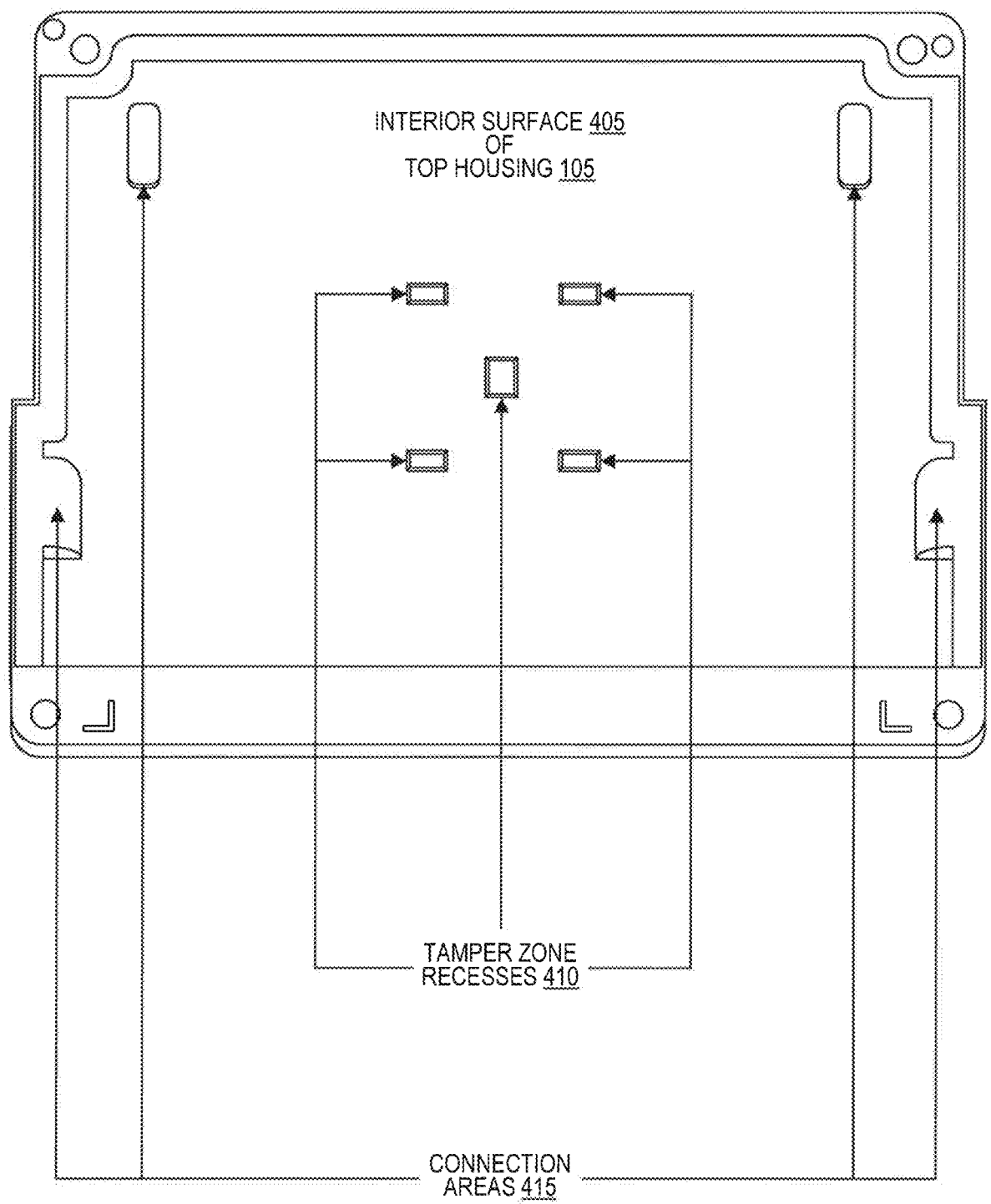
FIG. 4B illustrates an interior surface of the top housing with no conductive portions shown.

FIG. 4B illustrates an interior surface of the top housing with no conductive portions shown. The interior surface 405 of the top housing 105 of FIG. 4B includes connection areas 415. Endpoints of the tamper traces 420, also referred to as housing connection nodes, are positioned along the connection areas 415. In one implementation, the housing connection nodes are in a substrate layer different from the layer in which the guard rings are fabricated. This kind of sub-flush arrangement of nodes and guard ring prevents false positive detection of tampering.

The connection areas 415 can optionally be raised relative to the rest of the interior surface 405 so that the connection areas 415 are closer to the circuit board 100 than the rest of the interior surface 405 of the top housing 105.

The interior surface 405 of the top housing 105 of FIG. 4B includes tamper zone recesses 410. The tamper zone recesses 410 are recesses in the non-conductive portion of the top housing. The guard ring is in a substrate layer different from the layer in which the connection nodes are fabricated and is in in a cavity, referred to as guard ring recess. Tamper traces 420 running along the interior surface 405 dip into the tamper zone recesses 410. While the remainder of the interior surface 405 is coated with an insulative coating, the guard ring recess and the tamper zone recesses 410 are not, exposing the tamper traces 420. This allows voltage to be measured at different points along the tamper traces 420 via a multimeter or other type of voltage probe, allowing a "post-mortem" to be performed on a tampered-with system to identify a localized "tamper zone" in which the failure/tampering occurred, thereby identifying or helping to identify how the system was tampered with. The multimeter or voltage probe may be part of the circuit board 100, or directed by the circuit board, or may be separate from the system. In some cases, a voltage probe may be permanently coupled to each of the tamper zone recesses 410 for additional real-time monitoring of the tamper detection circuit 150 by the circuit board 100, for example by the board portion 155 of the tamper detection circuit 150.

FIG. 4C illustrates the interior surface of the top housing with an exemplary arrangement of tamper traces of varying voltages.

Some of the tamper traces 420 of FIG. 4C are illustrated using solid lines, while others are illustrated using dashed lines. These are illustrated differently to illustrate different voltages that the tamper traces 420 are configured to convey. The tamper traces 420 of FIG. 4C run through the tamper zone recesses 410 identified in FIG. 4B. The endpoints of the tamper traces 420, also referred to as housing connection nodes, are positioned along the connection areas 415 identified in FIG. 4B. The housing connection nodes are identified numerically in FIG. 4C, specifically numbered 460, 465, 470, 475, 480, 485, 490, and 495. In particular, one tamper trace 420 of FIG. 4C runs from housing connection node 460 to housing connection node 475. Another tamper trace 420 runs from housing connection node 465 to housing connection node 470. Another tamper trace 420 runs from housing connection node 480 to housing connection node 495. The last tamper trace 420 of FIG. 4C runs from housing connection node 485 to housing=connection node 490.

The tamper traces 420 of FIG. 4C are laid out to cover the entirety of the interior surface 405 of the housing 105, including the sidewall surfaces and the connection areas 415. The tamper traces 420 of FIG. 4C are laid out so that tamper traces 420 of different voltages run parallel to each other, so that a malicious party's metal drill bit boring through the housing 105 shorts out the tamper detection circuit 150 by connecting tamper traces 420 of differing voltages.

In one embodiment, the tamper traces 420 can be arranged to serve not only as part of the housing portion of the tamper detection circuit 150, but also simultaneously as an antenna 140 as described in relation to FIG. 1A or FIG. 4A. Such an antenna 140 can be any type of antenna 140 discussed with respect to FIG. 1A.

Figure 5:
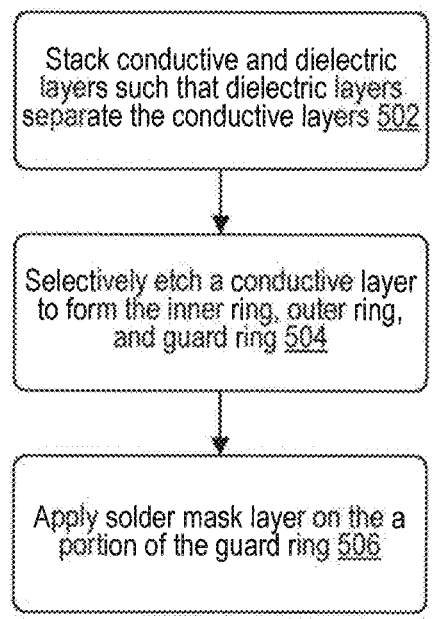
FIG. 5 is a flow diagram illustrating method of fabricating a sub-flush guard assembly, according to an embodiment of the present subject matter.

FIG. 5 is a flow diagram illustrating an exemplary method of fabrication of the guard ring, according to an embodiment of the present subject matter. A multilayer board includes, for example, copper foils, pre-impregnated and inner layer cores. Printed circuit board interconnection levels are built on top of a dielectric thin film layer. Circuitry features are formed using photolithographic and subtractive etch techniques, however additive techniques can also be used. The metallic foil and especially copper foil laminated to the substrate followed by using photolithographic and subtractive etching to create the circuitry. The copper foil includes a roughened or dendritic backside surface for inducing mechanical adhesion to the substrate. Smooth copper layers do not adequately bond without an auxiliary bonding agent. The pre-impregnated bonding sheets (prepreg), for example FR4, holds the cores together. During the lamination process, the resin in the prepreg is activated from pressure and heat. It flows across copper features and exposed laminate on the core and as it cools, the layers of foils and core bond.

According to one implementation, the method includes: a) providing a core with a plurality of conductive or copper layers, where each layer is separated by a layer of dielectric material or prepreg/FR4 material at step 502; b) exposing the copper contacts in a first copper layer to form conductive nodes (an inner ring and an outer ring) and guard ring by removing, for example by laser ablation, the dielectric material atop the first copper layer, ensuring that the inner, outer and the guard ring are separated by a predetermined gap at step 504; c) applying solder mask layer, such as a photo sensitive epoxy based ink, to at least part of the guard ring so as to prevent unintentional activation of the guard ring at step 506, and connecting a dome (such as one with connector pieces 160 and top housing 105) with the conductive nodes. Since the guard ring is now a different configuration from the conductive nodes, the unintentional activation is prevented.

Figure 6:
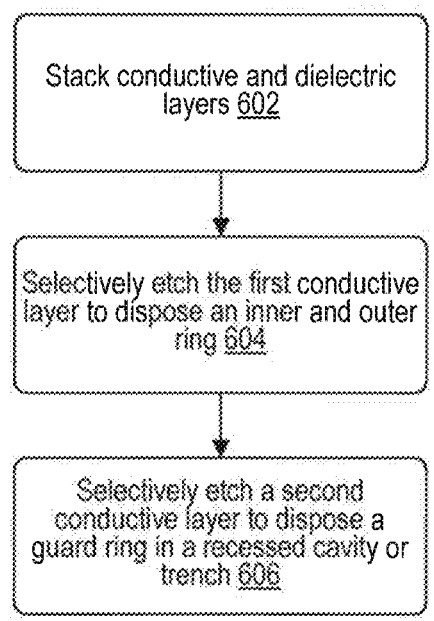
FIG. 6 is a flow diagram illustrating a method of fabricating a sub-flush guard assembly, according to another embodiment of the present subject matter.

FIG. 6 is a flow diagram illustrating one embodiment of a method of preventing unintentional activations of an additional sensor element, such as the guard ring by implementing a guard ring assembly including guard ring and sensor elements, such as conductive nodes, connection nodes or holder nodes. The method includes fabricating a guard ring assembly. As used herein, the term "trench" refers to a recess, which defines a conductor line in that the depth, length and width of a specific trench preferably have the same dimensions as the conductor to be formed in this trench by substantially filling such trench. The cross-section of the trenches and lands is preferably rectangular or has a groove (V)-shape, but may of course have any suitable shape.

The term "component recess" as used herein refers to a recess which serves to accommodate electronic components and for this purpose approximately has the same shape as the components. The components recesses preferably have a depth that is greater than the height of the electronic component to be able to embed the component in the dielectric layer. Electrically conducting structure elements may be formed in the component recesses to electrically connect the terminals on the electronic components to be inserted in such recesses to other conductor structures in the circuit plane. The cross-section and plan view of the component recesses is preferably rectangular but may of course be of any shape as required.

The term "via hole" as used herein refers to an aperture in the dielectric material which touches at least two circuit planes so that electrical connection may be made between these planes via such via hole. In most cases via holes only connect two such planes. If such a via hole is located at the outer side of the assembly, it will be a blind hole. If it is located between two layers which are situated beneath the outermost circuit plane it will be a buried hole. Via holes are preferably cylindrical but may also be V-shaped.

Apart from trenches and component recesses also via holes may be produced as three-dimensional structure elements in the dielectric layer by laser ablation or by any other means.

The present subject matter also contemplates guard rings to be in a different core as the conductive nodes. For example, in multi-core PCBs, the method of fabrication includes drilling a cavity or trench into a second core in which the guard ring is crafted. One of the ways to achieve this is through laser ablation and other such techniques. The flow diagram of FIG. 6 identifies a method of manufacturing an electronic circuit assembly, more specifically a printed circuit board (PCB) for a substantially sub-flush guard ring with respect to conductive nodes in a tamper detection circuit, according to an embodiment of the present subject matter. The following method steps are accomplished to manufacture the tamper detection sub-flush guard ring assembly: i) providing a substrate, the substrate comprising one or more dielectric layers as well as a plurality of conductive layers, such as copper layers, on at least one side thereof, ii) generating a structure at the surface of the substrate which corresponds to the direction where housing connection nodes are to be connected, iii) etching away the dielectric layer from the first layer to expose the conductive nodes, for example in a concentric ring (having different diameters) fashion, iv) selectively etching (for example by laser ablation) the first dielectric layer, prepreg layer, the second dielectric layer and the first copper layer between the inner and outer ring, such that the second copper layer is exposed and a trench or cavity is created with an exposed copper top in the second copper layer. Typically, the laser or plasma ablation is achieved by employing a focused laser beam to irradiate selected portions of the polymer surface. The energy of the focused laser beam removes the polymer by vaporizing and exploding away the material. Besides laser ablation, other techniques can be used to remove the material to expose off another conductive layer. Also, instead of removing material off of the layers, in some implementations, the embedded components, such as guard ring, can be created by deposition of material as well.

Figure 7A:
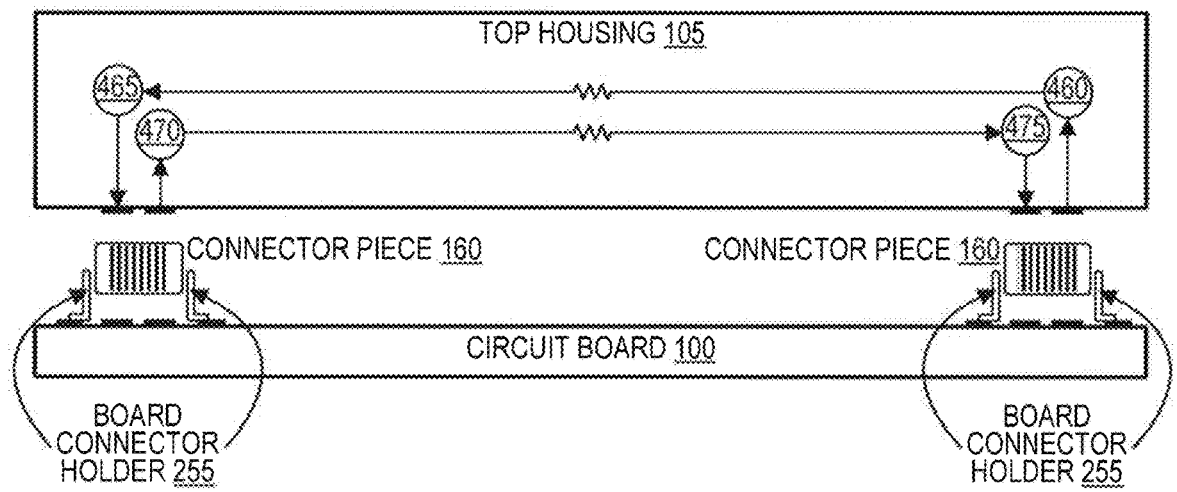
FIG. 7A is an exploded side view of a circuit board with board connector holders connecting to a top housing via connector pieces.

FIG. 7A is an exploded side view of a circuit board with board connector holders connecting to a top housing via connector pieces.

The exploded side view of FIG. 7A illustrates two tamper traces 420 and the direction in which current is flowing through them. The circuit board 100 of FIG. 7A includes board connector holders 255 keeping the connector pieces 160 in place between the circuit board 100 and the housing 105.

Figure 7B:
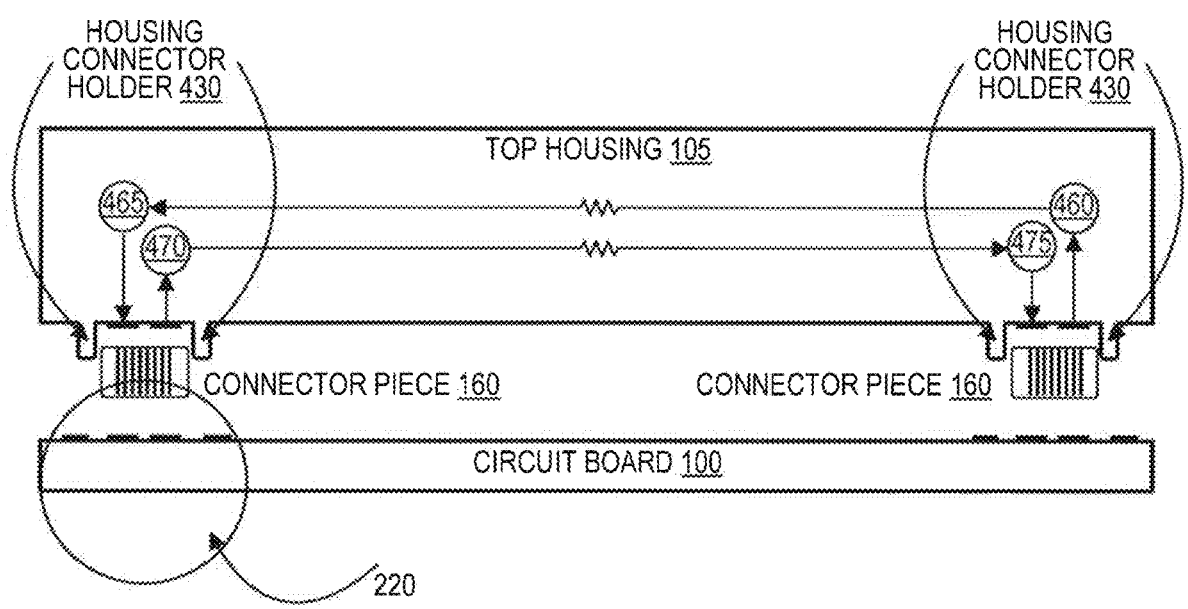
FIG. 7B is an exploded side view of a circuit board connecting to a top housing with housing connector holders via connector pieces.

FIG. 7B is an exploded side view of a circuit board connecting to a top housing with housing connector holders via connector pieces.

The exploded side view of FIG. 7B likewise illustrates two tamper traces 420 and the direction in which current is flowing through them. The circuit board 100 of FIG. 7A includes housing connector holders 430 keeping the connector pieces 160 in place between the circuit board 100 and the housing 105. The side view also illustrates the connection between the structure that includes guard ring 220 and the connection nodes 210 and the connector pieces 160. Even though the figure demonstrates a gap between the connection pieces 160 and the circuit board 160, it will be understood that they are connected to the housing 105 and in a depressed state to detect tampering. Further the guard ring 220 in the circled structure is on a different plane than the connection nodes 210.

Figure 8:
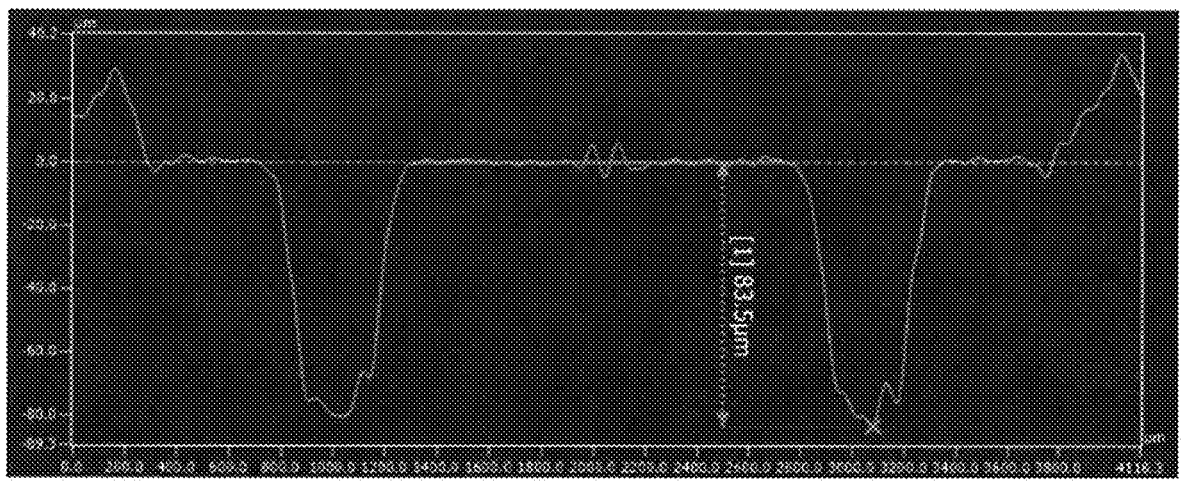
FIG. 8 is a graphical plot illustrating the gap between the guard ring and conductive nodes that are connected to the housing.

FIG. 8 illustrates a graphical plot showing the difference in height between the inner and outer rings and the guard rings. In one implementation, the depth of the guard ring recess is up to 80 microns. However, in some implementations, it can be less or more depending on the copper layer in which the guard ring is embedded.

Figure 9:
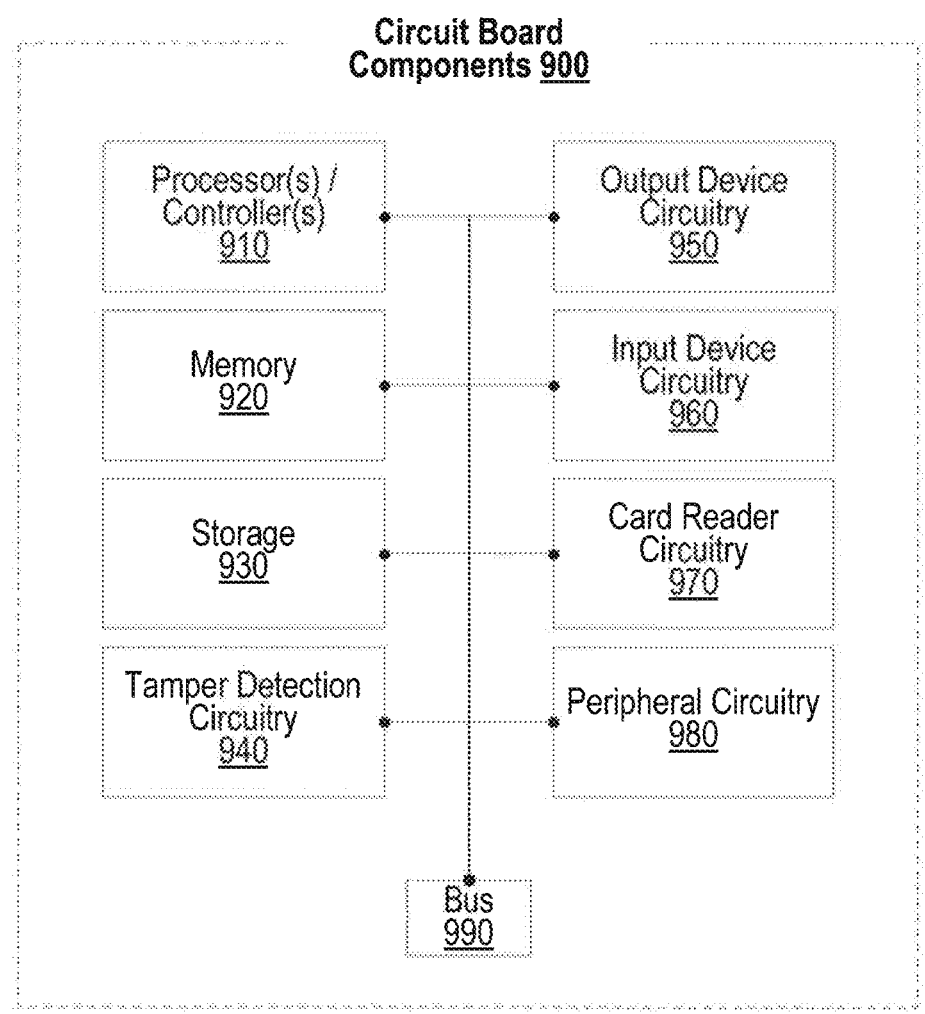
FIG. 9 is a block diagram of exemplary components that may be present on the circuit board, according to an embodiment of the present subject matter.

FIG. 9 illustrates exemplary circuit board components 900 that may be used to implement an embodiment of the present subject matter. The circuit board 100 described herein may include any combination of at least a subset of the circuit board components 900. In some embodiments, the circuit board 100 may actually include multiple circuit boards connected in a wired or wireless fashion, some of which may be at least partially enclosed by the security housing.

The circuit board components 900 of FIG. 9 may include one or more processors, controllers, or microcontrollers 910. These may in some cases aid in tamper detection, such as by performing at least some subset of the functions identified in FIG. 6. The circuit board components 900 of FIG. 9 may include one or more memory components 910 that may store, at least in part, instructions, executable code, or other data for execution or processing by the processor or controller 910. The memory components 910 may include, for example, cache memory, random access memory (RAM), read-only memory (ROM), or some other type of computer-readable storage medium.

The circuit board components 900 of FIG. 9 may further includes one or more computer-readable storage medium(s) 930 for storing data, such as a hard drive, magnetic disk drive, optical disk drive, flash memory, magnetic tape based memory, or another form of non-volatile storage. These may, for example, store credit card information, cryptographic keys, or other information, and may in some cases encrypt or decrypt such information with the aid of the processor or controller 910. The computer-readable storage medium(s) 930 may in some cases store, at least in part, instructions, executable code, or other data for execution or processing by the processor or controller 910.

The circuit board components 900 of FIG. 9 may include tamper detection circuitry 940, which may include any of the tamper detection circuit 150 discussed herein, and may include the board connector piece holder(s) 255 and any components discussed in FIG. 6.

The circuit board components 900 of FIG. 9 may include output device circuitry 950, which may include, for example, communication circuitry for outputting data through wired or wireless means, display circuitry for displaying data via a display screen, audio circuitry for playing audio via headphones or a speaker, printer circuitry for printing data via a printer, or some combination thereof. The display screen may be a liquid crystal display (LCD), a plasma display, an organic light-emitting diode (OLED) display, an electronic ink display, a projector-based display, a holographic display, or some combination thereof. The printer may be inkjet, laserjet, thermal, or some combination thereof. In some cases, the output device circuitry 950 may allow for transmission of data over a headphone audio jack, a microphone jack, BLUETOOTH™ wireless signal transfer, radio-frequency identification (RFID), near-field communications (NFC), 802.11 Wi-Fi, cellular network data transfer, or some combination thereof. The output device circuitry 950 may also include The circuit board components 900 of FIG. 9 may include input device circuitry 960, which may include, for example, communication circuitry for outputting data through wired or wireless means, microphone circuitry for receiving audio data, user interface circuitry for receiving user interface inputs, or some combination thereof, and may include variable pressure detection. Touchscreens may be capacitive, resistive, acoustic, or some combination thereof. In some cases, the input device circuitry 960 may allow receipt of data over a headphone audio jack, a microphone jack, BLUETOOTH™ wireless signal transfer, radio-frequency identification (RFID), near-field communications (NFC), 802.11 Wi-Fi, cellular network data transfer, or some combination thereof. Input device circuitry 960 may receive data from an alpha-numeric keypad or keyboard, a pointing device, a mouse, a trackball, a trackpad, a touchscreen, a stylus, cursor direction keys, or some combination thereof. The input device circuitry 960 may also receive data from the card reader circuitry 970.

The circuit board components 900 of FIG. 9 may include card reader circuitry 970, which may include components capable of reading information from a transaction card, or may include circuitry supporting components capable of reading information from a transaction card, with the actual card reader components located off of the circuit board 100. Card reader circuitry 970 may include, for example, a magnetic read head or other type of magnetic stripe reader that is capable of reading information from a magnetic stripe of a transaction card. Card reader circuitry 970 can also include an integrated circuit (IC) chip reader for reading an IC chip embedded in a transaction card. Such an IC chip can follow the Europay-Mastercard-Visa (EMV) payment IC chip standard. The IC chip reader can be contact-based, in that it can include one or more conductive prongs that contact a conductive metal contact pad of the IC chip. The IC chip can instead be contactless and use a contactless antenna. The contactless antenna can also double as a receiver for near-field-communication (NFC) signals, radio-frequency identification (RFID) signals, BLUETOOTH™ wireless signals, or some combination thereof, which can be sent from a transaction card or from a portable computing device.

Peripheral circuitry 980 may include any type circuitry permitting connection and use of computer support devices to add additional functionality to the circuit board 100. For example, peripheral circuitry 980 may support connection of a modem or a router. The components shown in FIG. 9 are depicted as being connected via a single bus 990. However, the components may be connected through one or more data transport means. For example, processor unit 910 and main memory 910 may be connected via a local microprocessor bus, and the storage medium 930, tamper detection circuitry 940, output device circuitry 950, input device circuitry 960, card reader circuitry 970, and peripheral circuitry 980 may be connected via one or more input/output (I/O) buses. As used herein, the term "approximately," "substantially, "and about" mean an amount close to the stated amount that still performs the desired function or achieves the desired result. Generally, the term "approximately, means an amount within 10% of the stated value.

The foregoing detailed description of the technology has been presented for purposes of illustration and description. It is not intended to be exhaustive or to limit the technology to the precise form disclosed. Many modifications and variations are possible in light of the above teaching. The described embodiments were chosen in order to best explain the principles of the technology, its practical application, and to enable others skilled in the art to utilize the technology in various embodiments and with various modifications as are suited to the particular use contemplated.

As a further example, variations of apparatus or process parameters (e.g., dimensions, configurations, components, process step order, etc.) may be made to further optimize the provided structures, devices and methods, as shown and described herein. In any event, the structures and devices, as well as the associated methods, described herein have many applications. Therefore, the disclosed subject matter should not be limited to any single embodiment described herein.

What is claimed is:

1. A system for preventing unintentional activation of a tamper detection circuit, the system comprising:
   a first sensor element of the tamper detection circuit disposed on a circuit board; and
   a guard ring of the tamper detection circuit disposed on the circuit board configured to be electrically isolated from the first sensor element in a first condition and to form an electrical connection with the first sensor element in a second condition, wherein the first condition is an untampered condition of the circuit board and the second condition is a tampered condition of the circuit board, the tampered condition being caused by an injection of a conductor into the tamper detection circuit, and wherein the guard ring is configured to be on a plane substantially different from the first sensor element to prevent unintentional activation of the tamper detection circuit.

2. The system of claim 1, further comprising:
   a non-conductive housing having the interior surface and an exterior surface, the interior surface configured to face the circuit board,
   a plurality of recesses along the interior surface of the non-conductive housing,
   the housing portion of the tamper detection circuit running along the interior surface of the non-conductive housing including over the plurality of recesses, the housing portion of the tamper detection circuit configured to connect to a board portion of the tamper detection circuit on the circuit board via the first sensor element and a second sensor element thereby completing the tamper detection circuit, the tamper detection circuit configured to detect tampering along the tamper detection circuit, and
   an insulative covering layered over a plurality of tamper traces other than over the plurality of recesses,
   wherein the housing portion of a tamper detection circuit includes a plurality of conductive tamper traces running along the interior surface of the non-conductive housing.

3. The system of claim 2, wherein the plurality of conductive tamper traces includes at least a first subset of conductive tamper traces configured to conduct a first voltage and a second subset of conductive tamper traces configured to conduct a second voltage.

4. The system of claim 1, wherein the tamper detection circuit is configured to detect tampering along the tamper detection circuit based on a plurality of measured voltages monitored at a plurality of monitor nodes of the tamper detection circuit.

5. The system of claim 1, wherein the tamper detection circuit is configured to disable one or more components of the circuit board upon detection of tampering.

6. The system of claim 1, wherein the guard ring is substantially sub-flushed with respect to the first sensor element.

7. The system of claim 1, wherein the guard ring is embedded in a substrate layer different from the first sensor element.

8. The system of claim 1, wherein depth of the guard ring is substantially smaller than the depth of the first sensor element.

9. The system of claim 1, further comprising a second sensor element, wherein the second sensor element, the first sensor element, and the guard ring form concentric circles such that the guard ring is between the first sensor element and the second sensor element.

10. The system of claim 1, wherein the security housing further comprises a plurality of housing connector piece holders protruding from the interior surface of a non-conductive housing, each housing connector piece holder configured to hold the first sensor element via a second sensor element.

11. The system of claim 1, wherein the security housing comprises a first security housing portion fused to a second security housing portion.

12. The system of claim 1, wherein the security housing includes a plurality of clip pockets along the exterior surface of the non-conductive housing, each clip pocket configured to receive a compression clip, each compression clip configured to compress a portion of the circuit board to a portion of the security housing.

13. The system of claim 1, wherein the unintentional activation of the first sensor element is triggered by modifying an electrical state between the guard ring and the first sensor element.

14. A system for preventing unintentional activation of a tamper detection circuit, the system comprising:
a housing;
a circuit board of the tamper detection circuit;
a first sensor element disposed on the circuit board of the tamper detection circuit; and
a second sensor element of the tamper detection circuit disposed on the circuit board and configured to be electrically isolated from the first sensor element in an untampered state of the tamper detection circuit and to form an electrical connection with the first sensor element in response to injection of a conductor indicative of a tampered state of the tamper detection circuit, wherein the second sensor element is configured to be on a first plane that differs from a second plane associated with the first sensor element to prevent unintentional activation of the tamper detection circuit.

15. The system of claim 14, further comprising:
a third sensor element disposed within an interior surface of the housing;
a plurality of recesses along the interior surface of the housing;
a housing portion of the tamper detection circuit running along the interior surface of the housing including over the plurality of recesses, the housing portion of the tamper detection circuit configured to connect to a board portion of the tamper detection circuit on the circuit board via the first sensor element and the third sensor element thereby completing the tamper detection circuit, the tamper detection circuit configured to detect tampering along the tamper detection circuit; and
an insulative covering layered over a plurality of tamper traces other than over the plurality of recesses.

16. The system of claim 15, wherein the plurality of conductive tamper traces includes at least a first subset of conductive tamper traces configured to conduct a first voltage and a second subset of conductive tamper traces configured to conduct a second voltage.

17. The system of claim 14, wherein the tamper detection circuit is configured to disable one or more components of the circuit board based at least in part on detection of tampering.

18. The system of claim 14, wherein the system further comprises:
a third sensor element disposed within an interior surface of the housing; and
a fourth sensor element, wherein the first sensor element, the second sensor element, and the fourth sensor element form concentric circles such that the second sensor element is between the first sensor element and the fourth sensor element.

19. A system for preventing unintentional activation of a tamper detection circuit, the system comprising:
a housing;
a circuit board of the tamper detection circuit;
a first sensor element disposed on the circuit board of the tamper detection circuit, the sensor element configured to be on a first plane; and
a second sensor element of the tamper detection circuit disposed on the circuit board and configured to be electrically isolated from the first sensor element in a first condition and to form an electrical connection with the first sensor element in a second condition, wherein the first condition is an untampered condition and the second condition is a tampered condition, the tampered condition being detected based on a conductor being within the tamper detection circuit, wherein the second sensor element is configured to be on a second plane in order to prevent unintentional activation of the tamper detection circuit.

20. The system of claim 19, further comprising:
a third sensor element disposed within an interior surface of the housing;
a plurality of recesses along the interior surface of the housing;
a housing portion of the tamper detection circuit running along the interior surface of the housing including over the plurality of recesses, the housing portion of the tamper detection circuit configured to connect to a board portion of the tamper detection circuit on the circuit board via the first sensor element and the third sensor element thereby completing the tamper detection circuit, the tamper detection circuit configured to detect tampering along the tamper detection circuit; and
an insulative covering layered over a plurality of tamper traces other than over the plurality of recesses.

* * * * *